United States Patent [19]

Rainer

[11] 4,317,823

[45] Mar. 2, 1982

[54] PYRAZOLOBENZODIAZEPINONES, THEIR INTERMEDIATES, THEIR COMPOSITIONS AND THEIR USE

[75] Inventor: Georg Rainer, Constance, Fed. Rep. of Germany

[73] Assignee: Byk Gulden Lomberg Chemische Fabrik GmbH, Constance, Fed. Rep. of Germany

[21] Appl. No.: 175,245

[22] Filed: Aug. 4, 1980

[30] Foreign Application Priority Data

Aug. 3, 1979 [CH] Switzerland .......................... 7128/79
Aug. 10, 1979 [CH] Switzerland .......................... 7333/79
Apr. 23, 1980 [CH] Switzerland .......................... 3149/80

[51] Int. Cl.³ .................... A61K 31/55; C07D 487/04; A61K 31/415
[52] U.S. Cl. ............................... 424/248.54; 424/250; 424/263; 424/273 R; 424/273 P; 260/239.3 T

[58] Field of Search ................................ 260/239.3 T; 424/248.54, 250, 273 R, 273 P, 263

[56] References Cited

U.S. PATENT DOCUMENTS 3,450,694  6/1969  Sweet et al. .................. 260/239.3 T
3,660,380  5/1972  Schmidt et al. .............. 260/239.3 T
3,743,734  7/1973  Schmidt et al ..................... 424/250

*Primary Examiner*—Robert T. Bond
*Attorney, Agent, or Firm*—Berman, Aisenberg & Platt

[57] ABSTRACT

1-(Lower)alkyl-4-(substituted)aminoalkylcarbonyl-1,4,9,10-tetrahydropyrazolo[4,3-b][1,5]benzodiazepin-10-ones are useful, e.g., to protect warm blooded animals against the formation of gastric ulcers. They are active ingredients in otherwise conventional medicament compositions administered enterally or parenterally in standard dosage forms. Their synthesis, their novel intermediates and their acid-addition salts are described.

15 Claims, No Drawings

PYRAZOLOBENZODIAZEPINONES, THEIR INTERMEDIATES, THEIR COMPOSITIONS AND THEIR USE

TECHNICAL FIELD

The invention relates to tetraazatricyclic compounds, their acid-addition salts, a process for their preparation, their intermediates, their use and medicaments containing them. The compounds are used in the treatment and prophylaxis of stomach and intestinal disorders in mammals, as intermediates and for the preparation of medicaments.

BACKGROUND

Pyridobenzodiazepines (which are stated to have ulcus inhibitory, secretion inhibitory, antitussive and, in part, antiemetic action) are claimed in German Auslegeschrift No. 1,795,183, whereas pyrazolobenzoxazepines and pyrazolobenzothiazepines (which are stated to have an anti-inflammatory and antipyretic action) are known from German Offenlegungsschrift No. 1,645,956. Pyrazolobenzoxazepines and pyrazolobenzothiazepines or pyrazolobenzodiazepines are considered in German Offenlegungsschrift No. 2,707,269 and in German Offenlegungsschrift No. 2,707,270, respectively, in which they are stated to have, in particular, a uricosuric and uricostatic activity, but also, in addition, analgesic, antiphlogistic, antidepressive, antiarrhythmic and diuretic effects.

SUMMARY OF THE INVENTION

Pyrazolobenzodiazepinones, a new class of compounds, have now been prepared. This new class possesses interesting pharmacological properties or provides compounds which are intermediates in the synthesis of those having such properties. The pharmacologically-active embodiments are used as such or in the form of medicament compositions for the treatment or prophylaxis of stomach or intestine disorders.

The new class of compounds comprises the following free bases:

(a) 1-(lower)alkyl-1,4,9,10-tetrahydropyrazolo[4,3-b][1,5]benzodiazepin-10-ones, (b) 1-(lower)alkyl-3-(lower)alkyl-1,4,9,10-tetrahydropyrazolo[4,3-b][1,5]benzodiazepin-10-ones, (c) 1-(lower)alkyl-4-(substituted)amino(lower)alkylcarbonyl-1,4,9,10-tetrahydropyrazolo[4,3-b][1,5]benzodiazepin-10-ones, (d) 1-(lower)alkyl-3-(lower)alkyl-4-(substituted)amino(lower)alkylcarbonyl-1,4,9,10-tetrahydropyrazolo[4,3-b][1,5]benzodiazepin-10-ones, (e) 1-(lower)alkyl-4-halo(lower)alkylcarbonyl-1,4,9,10-tetrahydropyrazolo[4,3-b][1,5]benzodiazepin-10-ones, and (f) 1-(lower)alkyl-3-(lower)alkyl-4-halo(lower)alkylcarbonyl-1,4,9,10-tetrahydropyrazolo[4,3-b][1,5]benzodiazepin-10-ones, and their acid-addition salts, particularly those which are pharmacologically acceptable.

DETAILS

The compounds are substituted pyrazolobenzodiazepinones of the formula

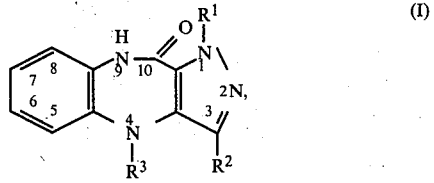

wherein $R^1$ denotes an alkyl radical with from 1 to 4 carbon atoms, $R^2$ denotes a hydrogen atom (—H) or an alkyl radical with from 1 to 4 carbon atoms, $R^3$ denotes a hydrogen atom (—H) or —CO—A—$R^4$, $R^4$ denotes halo (a halogen atom) or —N($R^5$)$R^6$, $R^5$ denotes an alkyl radical with from 1 to 4 carbon atoms or an alkenyl radical with from 3 to 5 carbon atoms, $R^6$ has one of the meanings of $R^5$, is —(CH$_2$)$_m$—N($R^7$)$R^8$, or $R^5$ and $R^6$, together with the nitrogen atom to which both are linked, denote a morpholino group, a pyrrolidino group, a piperidino group, a hexahydroazepin-1-yl group, a piperazin-1-yl group which is optionally substituted in the 4-position by a methyl, an ethyl or a benzyl group, a 2,4-dimethylpiperazin-1-yl group or a hexahydro-1H-1,4-diazepin-1-yl group which is substituted in the 4-position by a methyl or ethyl group, $R^7$ denotes an alkyl group with from 1 to 4 carbon atoms, $R^8$ denotes an alkyl group with from 1 to 4 carbon atoms, A denotes a straight-chain or branched alkylene group with from 1 to 5 carbon atoms and m denotes 2 or 3, and their acid-addition salts.

Alkyl radicals with from 1 to 4 carbon atoms are methyl, ethyl, propyl, isopropyl, n-butyl, isobutyl, sec.-butyl or tert.-butyl. Among the alkyl radicals, the methyl and ethyl radicals are preferred for $R^1$, $R^2$, $R^5$, $R^6$, $R^7$ and $R^8$. The methyl radical is particularly preferred as the alkyl radical of $R^1$ and $R^2$.

The allyl radical and the 2-methylallyl radical are illustrative of alkenyl radicals with from 3 to 5 carbon atoms.

Halogen atoms (Hal) are the iodine atom, the bromine atom and, especially, the chlorine atom.

Alkylene groups with from 1 to 5 carbon atoms comprise the trimethylene, tetramethylene, pentamethylene, 2-propylene or ethylmethylene group, preferably the ethylene group and especially the methylene group.

Any acid-addition salt is suitable. Particular mention is made of pharmacologically-acceptable salts of inorganic and of organic acids which are customarily used in medicine. Pharmacologically-unacceptable salts are converted into pharmacologically-acceptable salts by conventional processes. Examples of pharmacologically-acceptable salts are water-soluble or water-insoluble acid-addition salts, such as the hydrobromide, hydriodide, nitrate, acetate, benzoate, hibenzate [2-(4-hydroxybenzoyl)benzoate], fendizoate (2-[(2'-hydroxy-4-biphenylyl)carbonyl]benzoate), propionate, butyrate, sulfosalicylate, laurate, oxalate, amsonate (4,4'-diaminostilbene-2,2'-disulfonate), embonate [4,4'-methylene-bis-(3-hydroxy-2-naphthoate)], metembonate [4,4'-methylene-bis-(3-methoxy-2-naphthoate)], stearate, 2-hydroxy-3-naphthoate, 3-hydroxy-2-naphthoate and, especially, the hydrochloride, phosphate, sulfate, citrate, gluconate, maleate, malate, fumarate, succinate, tartrate, tosylate (p-toluenesulfonate), mesylate (methanesulfonate) or amidosulfonate.

Substituted pyrazolobenzodiazepinones I* of formula I, wherein
- $R^1$ denotes a methyl or ethyl radical,
- $R^2$ denotes a hydrogen atom (—H) or a methyl or ethyl radical,
- $R^3$ denotes a hydrogen atom (—H) or —CO—A—$R^4$,
- $R^4$ denotes a chlorine atom and
- A denotes a straight-chain or branched alkylene group with 1 or 2 carbon atoms, and their acid-addition salts are one embodiment of the invention.

Preferred representatives of the embodiment I* are those in which A denotes a methylene group.

Particularly preferred representative of embodiment I* are those in which $R^1$ denotes a methyl radical, $R^2$ denotes a hydrogen atom (—H) or a methyl or ethyl radical and $R^3$ denotes a hydrogen atom (—H) or —CO—CH$_2$—Cl, and also their acid-addition salts.

Substituted pyrazolobenzodiazepinones I** of formula I,
wherein
- $R^1$ denotes a methyl or ethyl radical,
- $R^2$ denotes a hydrogen atom (—H) or a methyl or ethyl radical,
- $R^3$ denotes —CO—A—$R^4$,
- $R^4$ denotes the group —N($R^5$)$R^6$ and
- $R^5$ denotes an alkyl radical with from 1 to 4 carbon atoms or an alkenyl radical with 3 or 4 carbon atoms and
- $R^6$ has one of the meanings of $R^5$, is —(CH$_2$)$_m$—N($R^7$)$R^8$, or
- $R^5$ and $R^6$, together with the nitrogen atom to which both are linked, denote a morpholino group, a pyrrolidino group, a piperidino group, a hexahydroazepin-1-yl group, a piperazin-1-yl group which is substituted in the 4-position by a methyl, ethyl or benzyl group, a 2,4-dimethylpiperazin-1-yl group or a hexahydro-1H-1,4-diazepin-1-yl group which is substituted in the 4-position by a methyl or ethyl group,
- $R^7$ denotes a methyl or ethyl group,
- $R^8$ denotes a methyl or ethyl group,
- m denotes 2 or 3 and
- A denotes a straight-chain or branched alkylene group with 1 or 2 carbon atoms, and their acid-addition salts, comprise a further embodiment of the invention.

One group of representatives of embodiment I** is constituted by those in which $R_1$ denotes a methyl or ethyl radical; $R^2$ denotes a hydrogen atom (—H) or a methyl or ethyl radical; $R^5$ denotes a methyl or ethyl radical; and $R^6$ has the meaning of $R^5$ or represents the group —(CH$_2$)$_m$—N($R^7$)$R^8$; or $R^5$ and $R^6$, together with the nitrogen atom to which both are bound, denote a pyrrolidino, piperidino of hexahydroazepin-1-yl radical; each of $R^7$ and $R^8$ denotes a methyl or ethyl radical; m denotes 2; and A denotes a methylene group; and also their pharmacologically-acceptable acid-addition salts.

Another group of representatives of embodiment I** is constituted by those in which $R^1$ denotes a methyl or ethyl radical; $R^2$ denotes a hydrogen atom (—H) or a methyl or ethyl radical; $R^5$ and $R^6$, together with the nitrogen atom to which both are bound, denote a piperazin-1-yl group which is substituted in the 4-position by a methyl, ethyl or benzyl group, a 2,4-dimethylpiperazin-1-yl group or a hexahydro-1H-1,4-diazepin-1-yl group which is substituted in the 4-position by a methyl or ethyl group; and A denotes a methylene group; and also their pharmacologically-acceptable acid-addition salts.

Preferred representatives of the embodiment I** are those in which $R^1$ denotes a methyl or ethyl radical; $R^2$ denotes a hydrogen atom (—H) or a methyl or ethyl radical; $R^5$ and $R^6$, together with the nitrogen atom to which both are bound, denote a piperazin-1-yl group which is substituted in the 4-position by a methyl group; and A denotes a methylene group; and also their pharmacologically-acceptable acid-addition salts.

The representative of embodiment I** in which each of $R^1$ and $R^2$ denote a methyl radical; $R^5$ and $R^6$, together with the nitrogen atom to which both are bound, denote a piperazin-1-yl group which is substituted in the 4-position by a methyl group; and A denotes a methylene group; and also its pharmacologically-acceptable acid-addition salts, are particularly preferred.

The following are illustrative examples of compounds according to the invention:
4-[2-{di-(n-propyl)amino}propionyl]-1,3-dimethyl-1,4,9,10-tetrahydropyrazolo[4,3-b][1,5]benzodiazepin-10-one,
4-[4-{di-(n-butyl)amino}butyryl]-1,3-dimethyl-1,4,9,10-tetrahydropyrazolo[4,3-b][1,5]benzodiazepin-10-one,
4-[2-(diethylamino)propionyl]-1,3-dimethyl-1,4,9,10-tetrahydropyrazolo[4,3-b][1,5]benzodiazepin-10-one,
4-[5-(diisopropylamino)valeryl]-1,3-dimethyl-1,4,9,10-tetrahydropyrazolo[4,3-b][1,5]benzodiazepin-10-one,
4-diisobutylaminoacetyl-1,3-diethyl-1,4,9,10-tetrahydropyrazolo[4,3-b][1,5]benzodiazepin-10-one,
4-[N-(n-butyl)-N-(tert.-butyl)aminoacetyl]-1-ethyl-1,4,9,10-tetrahydropyrazolo[4,3-b][1,5]benzodiazepin-10-one,
4-[4-(diallylamino)butyryl]-1,3-dimethyl-1,4,9,10-tetrahydropyrazolo[4,3-b][1,5]benzodiazepin-10-one,
4-[di-(sec.-butyl)aminoacetyl]-1-ethyl-3-methyl-1,4,9,10-tetrahydropyrazolo[4,3-b][1,5]benzodiazepin-10-one,
4-[2-{N-ethyl-n-(n-butyl)amino}propionyl]-1,3-dimethyl-1,4,9,10-tetrahydropyrazolo[4,3-b][1,5]benzodiazepin-10-one,
1,3-dimethyl-4-[5-{N-methyl-N-(n-butyl)amino}-valeryl]-1,4,9,10-tetrahydropyrazolo[4,3-b][1,5]benzodiazepin-10-one,
1-methyl-4-[N-methyl-N-(sec.-butyl)aminoacetyl]-1,4,9,10-tetrahydropyrazolo[4,3-b][1,5]benzodiazepin-10-one,
1,3-dimethyl-4-[5-{N-methyl-N-(tert.-butyl)amino}-valeryl]-1,4,9,10-tetrahydropyrazolo[4,3-b][1,5]benzodiazepin-10-one,
1,3-dimethyl-4-[2-piperidinopropionyl]-1,4,9,10-tetrahydropyrazolo[4,3-b][1,5]benzodiazepin-10-one,
4-[4-(hexahydroazepin-1-yl)butyryl]-1,3-dimethyl-1,4,9,10-tetrahydropyrazolo[4,3-b][1,5]benzodiazepin-10-one,
4-[3-{di-(n-butyl)amino}propionyl]-1,3-dimethyl-1,4,9,10-tetrahydropyrazolo[4,3-b][1,5]benzodiazepin-10-one,
4-[3-(diallylamino)propionyl]-1,3-dimethyl-1,4,9,10-tetrahydropyrazolo[4,3-b][1,5]benzodiazepin-10-one, 4-[3-{di-(sec.-butyl)amino}propionyl]-1,3-dimethyl-1,4,9,10-tetrahydropyrazolo[4,3-b][1,5]benzodiazepin-10-one, 4-[3-{N-(n-butyl)-N-(tert.-butyl)amino}propionyl]-1,3-dimethyl-1,4,9,10-tetrahydropyrazolo[4,3-b][1,5]benzodiazepin-10-one, 4-[3-{N-ethyl-N-(n-butyl)amino}propionyl]-1,3-dimethyl-1,4,9,10-tetrahydropyrazolo[4,3-b][1,5]benzodiazepin-10-one, 1,3-dimethyl-4-[3-{N-methyl-N-(sec.-butyl)amino}propionyl]-1,4,9,10-tetrahydropyrazolo[4,3-b][1,5-benzodiazepin-10-one, 1,3-dimethyl-4-[3-piperidinopropionyl]-1,4,9,10-tetrahydropyrazolo[4,3-b][1,5]benzodiazepin-10-one, 1-methyl-4-[(4-methylpiperazin-1-yl)acetyl]-3-propyl-1,4,9,10-tetrahydropyrazolo[4,3-b][1,5]benzodiazepin-10-one, 1,3-dimethyl-4-[2-(dimethylamino)propionyl]-1,4,9,10-tetrahydropyrazolo[4,3-b][1,5]benzodiazepin-10-one, 4-[(N-ethyl-N-methallylamino)acetyl]-1-methyl-1,4,9,10-tetrahydropyrazolo[4,3-b][1,5]benzodiazepin-10-one, 4-[2-(N-allyl-N-methylamino)propionyl]-1-ethyl-1,4,9,10-tetrahydropyrazolo[4,3-b][1,5]benzodiazepin-10-one, 4-[(N-allyl-N-propylamino)acetyl]-1,3-dibutyl-1,4,9,10-tetrahydropyrazolo[4,3-b][1,5]benzodiazepin-10-one, 1-ethyl-4-[2-(N-methallyl-N-methylamino)propionyl]-3-propyl-1,4,9,10-tetrahydropyrazolo[4,3-b][1,5]benzodiazepin-10-one, 4-[3-(dimethallylamino)propionyl]-1-isopropyl-1,4,9,10-tetrahydropyrazolo[4,3-b][1,5]benzodiazepin-10-one, 4-[2-(N-allyl-N-methallylamino)propionyl]-1-ethyl-1,4,9,10-tetrahydropyrazolo[4,3-b][1,5]benzodiazepin-10-one, 4-[2-(diallylamino)propionyl]-3-ethyl-1-methyl-1,4,9,10-tetrahydropyrazolo[4,3-b][1,5]benzodiazepin-10-one, 4-[{N-(2-diethylaminoethyl)-N-ethylamino}acetyl]-1-isopropyl-1,4,9,10-tetrahydropyrazolo[4,3-b][1,5]benzodiazepin-10-one, 4-[2-{N-(2-dimethylaminoethyl)-N-ethylamino}propionyl]-1-methyl-1,4,9,10-tetrahydropyrazolo[4,3-b][1,5]benzodiazepin-10-one, 1-(n-butyl)-4-[2-{N-(2-diethylaminoethyl)-N-methylamino}propionyl]-3-ethyl-1,4,9,10-tetrahydropyrazolo[4,3-b][1,5]benzodiazepin-10-one, 4-[{N-(2-dimethylaminoethyl)-N-methallylamino}acetyl]-1-methyl-1,4,9,10-tetrahydropyrazolo[4,3-b][1,5]benzodiazepin-10-one, 4-[2-{N-allyl-N-(2-diethylaminoethyl)amino}propionyl]-1-isobutyl-1,4,9,10-tetrahydropyrazolo[4,3-b][1,5]benzodiazepin-10-one, 1,3-dimethyl-4-[{N-(2-diisopropylaminoethyl)-N-methallylamino}acetyl]-1,4,9,10-tetrahydropyrazolo[4,3-b][1,5]benzodiazepin-10-one, 4-[2-{N-allyl-N(2-dimethylaminoethyl)amino}propionyl]-1-ethyl-3-methyl-1,4,9,10-tetrahydropyrazolo[4,3-b][1,5]benzodiazepin-10-one, 1-methyl-4-(2-morpholinopropionyl)-1,4,9,10-tetrahydropyrazolo[4,3-b][1,5]benzodiazepin-10-one, 4-(3-piperidinopropionyl)-1-(n-propyl)-1,4,9,10-tetrahydropyrazolo[4,3-b][1,5]benzodiazepin-10-one, 1-ethyl-4-[hexahydroazepin-1-yl)acetyl]-1,4,9,10-tetrahydropyrazolo[4,3-b][1,5]benzodiazepin-10-one, 1-isopropyl-4-[4-(piperazin-1-yl)butyryl]-1,4,9,10-tetrahydropyrazolo[4,3-b][1,5]benzodiazepin-10-one, 4-[3-(4-benzylpiperazin-1-yl)butyryl]-1-ethyl-1,4,9,10-tetrahydropyrazolo[4,3-b][1,5]benzodiazepin-10-one, 1-methyl-4-[4-methyl(hexahydro-1H-1,4-diazepin-1-yl)acetyl]-1,4,9,10-tetrahydropyrazolo[4,3-b][1,5]benzodiazepin-10-one, 4-[2-{4-ethyl(hexahydro-1H-1,4-diazepin-1-yl)}propionyl]-1-propyl-1,4,9,10-tetrahydropyrazolo[4,3-b][1,5]benzodiazepin-10-one, 1,3-diethyl-4-[3-{4-ethyl(hexahydro-1H-1,4-diazepin-1-yl)}propionyl]-1,4,9,10-tetrahydropyrazolo[4,3-b][1,5]benzodiazepin-10-one, 3-butyl-1-methyl-4-[(4-methylpiperazin-1-yl)acetyl]-1,4,9,10-tetrahydropyrazolo[4,3-b][1,5]benzodiazepin-10-one, 4-[3-(hexahydroazepin-1-yl)propionyl]-1,3-dimethyl-1,4,9,10-tetrahydropyrazolo[4,3-b][1,5]benzodiazepin-10-one, 4-bromoacetyl-1,3-dimethyl-1,4,9,10-tetrahydropyrazolo[4,3-b][1,5]benzodiazepin-10-one, 4-iodoacetyl-1,3-dimethyl-1,4,9,10-tetrahydropyrazolo[4,3-b][1,5]benzodiazepin-10-one, 4-[3-bromopropionyl]-1,3-dimethyl-1,4,9,10-tetrahydropyrazolo[4,3-b][1,5]benzodiazepin-10-one, 4-[3-iodopropionyl]-1,3-dimethyl-1,4,9,10-tetrahydropyrazolo[4,3-b][1,5]benzodiazepin-10-one, 4-[chloroacetyl]-1,3-diethyl-1,4,9,10-tetrahydropyrazolo[4,3-b][1,5]benzodiazepin-10-one and, preferably, 1,3-dimethyl-4-[(4-methylpiperazin-1-yl)acetyl]-1,4,9,10-tetrahydropyrazolo[4,3-b][1,5]benzodiazepin-10-one, 1,3-dimethyl-1,4,9,10-tetrahydropyrazolo[4,3-b][1,5]benzodiazepin-10-one and 4-chloroacetyl-1,3-dimethyl-1,4,9,10-tetrahydropyrazolo[4,3-b][1,5]benzodiazepin-10-one.

The substituted pyrazolobenzodiazepinones of formula I and their acid-addition salts and embodiments I* and I possess valuable properties which make them industrially useful. The substituted pyrazolobenzodiazepinones of formula I [in which $R^3$ denotes $-CO-A-N(R^5)R^6$, and A, $R^5$ and $R^6$ have their previously-ascribed meanings] and those of embodiment I are characterized by imparting to warmblooded animals (to which they are administered) an excellent protective action for the stomach and intestines; they inhibit, for example, the formation of gastric ulcers. Furthermore, in view of their low toxicity and the absence of appreciable side-effects, they have an advantageous therapeutic range. Moreover, the compounds have only a slight anticholinergic action. The substituted pyrazolobenzodiazepinones of formula I [in which $R^3$ denotes a hydrogen atom (—H) or —CO—A—Hal, and A and Hal have their noted meanings] and those of embodiment I* are valuable intermediate products in the preparation of the pharmacologically-active and therapeutically-usable compounds according to the invention.

The excellent activity of the pharmacologically-active substituted pyrazolobenzodiazepinones and their pharmacologically-, that is biologically-, acceptable acid-addition salts make it possible to use them in human medicine and also in veterinary medicine, wherein they are used for the treatment and prophylaxis of diseases caused by affections of the stomach or intestines. For example, acute and chronic ulcus ventriculi and ulcus duodeni, gastritis or hyperacid irritation of the stomach in humans or animals are thus treated.

The invention also relates, therefore, to a process for the treatment of mammals affected by one of the previously-mentioned diseases. The process is characterized by administering a therapeutically-effective and pharmacologically-acceptable quantity of one or more compounds of formula I, preferred representatives thereof and/or salts thereof to an affected mammal.

The invention additionally relates to the use of compounds according to the invention in combating the indicated diseases. The invention also includes the use of compounds according to the invention in the preparation of medicaments which are employed for combating the mentioned diseases.

The invention further concerns medicaments containing one or more pyrazolobenzodiazepinones Ia of formula I, wherein $R^1$ denotes an alkyl radical with from 1 to 4 carbon atoms, $R^2$ denotes a hydrogen atom (—H) or an alkyl radical with from 1 to 4 carbon atoms, $R^3$ denotes —CO—A—$R^4$, $R^4$ denotes —N($R^5$)$R^6$ and $R^5$ denotes an alkyl radical with from 1 to 4 carbon atoms or an alkenyl radical with from 3 to 5 carbon atoms, $R^6$ has one of the meanings of $R^5$, is —(CH$_2$)$_m$—N($R^7$)$R^8$, or $R^5$ and $R^6$, together with the nitrogen atom to which both are linked, denote a morpholino group, a pyrrolidino group, a piperidino group, a hexahydroazepin-1-yl group, a piperazin-1-yl group which is optionally substituted in the 4-position by a methyl, ethyl or benzyl group, a 2,4-dimethylpiperazin-1-yl group or a hexahydro-1H-1,4-diazepin-1-yl group which is substituted in the 4-position by a methyl or ethyl group, $R^7$ denotes an alkyl group with from 1 to 4 carbon atoms, $R^8$ denotes an alkyl group with from 1 to 4 carbon atoms, A denotes a straight-chain or branched alkylene group with from 1 to 5 carbon atoms and m denotes 2 or 3, and/or their pharmacologically-acceptable acid-addition salts.

The embodiments of the medicaments are those containing pyrazolobenzodiazepinones I** or preferred representatives thereof and/or pharmacologically-acceptable acid-addition salts thereof.

The medicaments are prepared by known processes. The compounds according to the invention are employed as medicaments either on their own or, preferably, in combination with suitable pharmaceutical excipients. When the new pharmaceutical formulations contain pharmaceutical excipients in addition to a compound according to the invention, the content of active compound in these mixtures is from 0.5 to 95, preferably from 15 to 75, percent by weight of the total mixture.

In accordance with the invention, the active compounds are used in the field of human and veterinary medicine in any desired form, provided that the establishment and/or maintenance of sufficient blood and tissue levels of active compound are ensured. This is achieved, for example, by oral, rectal or parenteral administration in suitable doses. The pharmaceutical formulation of active compound is customarily in the form of unit doses appropriate for the desired mode of administration. A unit dose is, for example, a tablet, a dragee, a capsule, a suppository or a measured volume of a powder, of a granular material, of a solution, of an emulsion or of a suspension.

"Unit dose" in the context of the present invention means a physically-determined unit which contains an individual amount of the active ingredient in combination with a pharmaceutical excipient, the content of active compound in the unit dose corresponding to a fraction or multiple of the therapeutic individual dose. An individual dose preferably contains the amount of active compound which is given in one administration and usually corresponds to a whole daily dose or a half, one third or one quarter of the daily dose. If only a fraction, such as a half or one quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain from about 0.1 to 500, advantageously from 0.5 to 100 and particularly from 1 to 30, mg of active compound.

In general, it is advantageous in human medicine to administer the active compound or compounds, when these are given orally, in a daily dose of from about 0.01 to about 5, preferably from 0.05 to 2.5, and particularly from 0.1 to 1.5, mg/kg of body weight, optionally in the form of several, preferably from 1 to 3, individual administration to achieve the desired results. An individual administration contains the active compound or compounds in amounts of from about 0.01 to about 2.5, preferably from 0.01 to 1.5 and particularly from 0.05 to 0.5, mg/kg of body weight. Similar dosages are used in the case of parenteral, for example intravenous, treatment.

The pharmaceutical formulation is administered, for therapeutical purposes, 1 to 4 times daily at fixed or varying points in time, for example before each meal and/or in the evening. It can, however, be necessary to deviate from the indicated dosages and, in particular, to do so in accordance with the nature, body weight and age of the patient being treated, the nature and severity of the illness, the nature of the formulation and of the administration of the medicament, the frequency of administration, and the time or interval over which administration takes place. Thus, in some cases, less than the stated amount of active compound is sufficient, while it is necessary to exceed such amount of active compound in other cases.

The optimum dosage and method of administration of the active compounds required in each particular case is determined by the expert in accordance with his expert knowledge.

The pharmaceutical formulations preferably consist of the active compounds according to the invention and nontoxic, pharmaceutically-acceptable medicinal excipients, which are used as an admixture or diluent in solid, semisolid or liquid form, or as a means of encasing, for example in the form of a capsule, a tablet coating, a sachet or some other container for the therapeutically active ingredient. An excipient can, for example, serve as a promoter of the resorption of the medicament by the body, as a formulating auxiliary, as a sweetener, as a flavor correctant, as a colorant or as a preservative.

Examples of dosage forms which are used orally are tablets, dragees, hard and soft capsules, for example capsules made of gelatin, dispersible powders, granules, aqueous and oily suspensions, emulsions, solutions or syrups.

Tablets contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. If desired, the tablets are additionally provided with a coating, which optionally delays dissolution and resorption of the medicament in the gastrointestinal tract and hence provides, for example, better toleration, a protracted effect or a delayed effect. Gelatin capsules generally contain the medicament mixed with a diluent, for example a solid diluent, such as calcium carbonate or kaolin, or an oily diluent, such as neutral oil, olive oil, groundnut oil or paraffin oil.

Aqueous suspensions ordinarily contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitol monooleate, polyoxyethylene sorbitan monooleate or lecithin; preservatives, for example methyl hydroxybenzoate or propyl hydroxybenzoate; flavoring agents; and sweeteners, for example sucrose, lactose, sodium cyclamate, dextrose or invert sugar syrup.

Oily suspensions contain, for example, groundnut oil, olive oil, sesame oil, coconut oil or paraffin oil and thickeners, such as beeswax, hard paraffin or cetyl alcohol; and also sweeteners, flavoring agents and antioxidants.

Emulsions contain, for example, olive oil, groundnut oil or paraffin oil, as well as emulsifiers, such as gum acacia, gum tragacanth, phosphatides, sorbitan monooleate and polyoxyethylene sorbitan monooleate, and sweeteners and flavoring agents.

For rectal administration of the medicaments, suppositories (which are prepared with the aid of binders which melt at the rectal temperature, for example cacao butter or polyethylene glycol) are used.

For parenteral administration of the medicaments, sterile injectable aqueous suspensions, isotonic salt solutions or other solutions which contain dispersing agents or wetting agents and/or pharmaceutically-acceptable diluents, for example propylene glycol or butylene glycol, are used.

The active compound or compounds are optionally employed in a micro-encapsulated form, if appropriate together with one or more of the indicated excipients or additives.

When the substituted pyrazolobenzodiazepinones according to the invention and/or their pharmacologically-acceptable acid-addition salts are employed for treating the indicated diseases, the pharmaceutical formulations optionally contain one or more pharmacologically-active constituents from other groups of medicaments, such as antiacids, for example aluminum hydroxide or magnesium aluminate; secretion inhibitors, such as $H_2$-blockers, for example cimetidine; therapeutic agents for the stomach and intestines, for example metoclopramide, bromopride or tiapride; tranquilizers, such as benzodiazepines, for example diazepam; spasmolytic agents, for example bietamiverine or camylofin; anticholinergic agents, for example oxyphencyclimine or phencarbamide; glucocorticoids, such as prednisolone, fluocortolone or betamethasone; nonsteroidal antiphlogistic agents, such as arylacetic acids and arylpropionic acids, heteroarylacetic acids and heteroarylpropionic acids, benzothiazinecarboxamide dioxides, pyrazolidinediones and quinazolinones, for example ibuprofen, naproxen, diclofenac, fenbufen, indomethacin, lonazolac, sudoxicum, piroxicam, phenylbutazone, bumadizone calcium and proquazone; local anaesthetics, for example tetracaine or procaine; and, if appropriate, also ferments, vitamins, aminoacids and the like.

The invention furthermore relates to a process for the preparation of the substituted pyrazolobenzodiazepinones of formula I, wherein $R^1$ denotes an alkyl radical with from 1 to 4 carbon atoms, $R^2$ denotes a hydrogen atom (—H) or an alkyl radical with from 1 to 4 carbon atoms, $R^3$ denotes a hydrogen atom (—H) or —CO—A—$R^4$, $R^4$ denotes halo or —N($R^5$)$R^6$, $R^5$ denotes an alkyl radical with from 1 to 4 carbon atoms or an alkenyl radical with from 3 to 5 carbon atoms, $R^6$ has one of the meanings of $R^5$, is —(CH$_2$)$_m$—N($R^7$)$R^8$, or $R^5$ and $R^6$, together with the nitrogen atom to which both are linked, denote a morpholino group, a pyrrolidino group, a piperidino group, a hexahydroazepin-1-yl group, a piperazin-1-yl group which is optionally substituted in the 4-position by a methyl, ethyl or benzyl group, a 2,4-dimethylpiperazin-1-yl group or a hexahydro-1H-1,4-diazepin-1-yl group which is substituted in the 4-position by a methyl or ethyl group, $R^7$ denotes an alkyl group with from 1 to 4 carbon atoms, $R^8$ denotes an alkyl group with from 1 to 4 carbon atoms, A denotes a straight-chain or branched alkylene group with from 1 to 5 carbon atoms and m denotes 2 or 3, and also their acid-addition salts.

The process is characterized by cyclizing anilinopyrazolecarboxylic acid derivatives of the formula

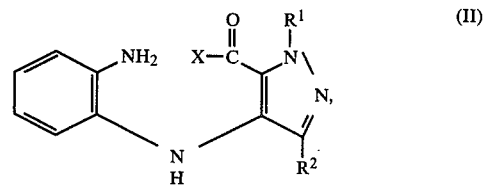

wherein $R^1$ and $R^2$ have their previously-ascribed meanings and

X denotes a leaving group, with the elimination of a compound HX and, when appropriate, replacing (in the resulting reaction product of formula I, wherein $R^3$ denotes a hydrogen atom) the hydrogen atom by a —CO—A—$R^4$ group, and/or converting resulting bases into acid-addition salts or resulting acid-addition salts into the corresponding free base or into a pharmacologically-acceptable acid-addition salt.

X preferably represents an —OH group, an —O—$R^9$ group or an —N($R^{10}$)$R^{11}$ group, wherein $R^9$ denotes an alkyl group, a cycloalkyl group, an optionally-substituted aralkyl group or an optionally-substituted aryl group, $R^{10}$ denotes a hydrogen atom (—H), an alkyl group, a cycloalkyl group, an optionally-substituted aralkyl group or an optionally-substituted aryl group and $R^{11}$ has one of the meanings of $R^{10}$, or $R^{10}$ and $R^{11}$, together with the nitrogen atom to which both are linked, denote an optionally-substituted, non-aromatic, heterocyclic radical.

Suitable alkyl radicals $R^9$, $R^{10}$ and $R^{11}$ are straight-chain or branched alkyl groups with from 1 to 11, preferably from 1 to 5, carbon atoms.

Suitable cycloalkyl groups are those with from 3 to 9, preferably from 5 to 8, carbon atoms.

Possible aralkyl groups are those with aryl groups containing up to 12 carbon atoms and alkyl groups containing from 1 to 4 carbon atoms, amongst which those having 6 carbon atoms in the aryl radical and from 1 to 4 carbon atoms in the alkyl radical, above all with 1 carbon atom in the alkyl radical, are preferred. Examples include the benzyl, phenethyl and phenylpropyl groups, of which the benzyl group is preferred. The aralkyl groups are also optionally substituted; those which are monosubstituted in the aryl radical, inter alia, by halogen atoms, such as fluorine, chlorine or bromine atoms, or alkyl and/or alkoxy groups with from 1 to 4 carbon atoms are preferred. Examples include the 4-chlorobenzyl group, the 3-chlorobenzyl group, the 4-bromobenzyl group, the 2-fluorobenzyl group, the 4-fluorobenzyl group, the 4-methylbenzyl group and the 4-methoxybenzyl group.

Contemplated aryl radicals, which are optionally substituted, are those with from 6 to 10 carbon atoms, for example the phenyl or naphthyl radical, especially the phenyl radical. Substitution of substituted aryl radicals is in any desired position, for example, by 2 substituents or, preferably, by 1 substituent, and the energetically-favored positions are preferred. Exemplary substituents are, inter alia, halogen atoms, for example fluorine and bromine, but preferably chlorine, or alkyl or alkoxy groups with from 1 to 4 carbon atoms in each case. Examples of substituted aryl groups are the 2-chlorophenyl, 3-chlorophenyl, 4-chlorophenyl, 3-bromophenyl, 4-bromophenyl, 4-fluorophenyl, 3-methylphenyl, 4-methylphenyl, 3,4-dichlorophenyl, 3-chloro-4-methylphenyl, 4-methoxyphenyl, 4-ethoxyphenyl, 3,4-dimethoxyphenyl, cumenyl and 4-chloro-1-naphthyl groups, of which the halo-substituted phenyl groups are preferred.

Aryl and aralkyl groups optionally have ring heteroatoms, for example nitrogen, oxygen or sulfur atoms. Examples include the 3-pyridyl radical, the 2-(1-phenyl-4-pyrazolyl)ethyl radical and the 2-methyl-5-benzthiazolyl radical.

Suitable non-aromatic heterocyclic radicals are those which are derived from saturated and unsaturated heterocyclic structures. Examples are the morpholino group; the thiomorpholino group; the pyrrolidino group; the piperidino group; the piperazino group; the hexahydroazepin-1-yl group; the hexahydro-1H-1,4-diazepin-1-yl group; a 4-alkylpiperazin-1-yl or 4-aralkylpiperazin-1-yl group, such as the 4-methyl- or 4-ethyl- or 4-benzylpiperazin-1-yl group; a dialkylpiperazin-1-yl group, such as the 2,4-dimethylpiperazin-1-yl group; a 4-alkylhexahydro-1H-1,4-diazepin-1-yl or 4-aralkylhexahydro-1H-1,4-diazepin-1-yl group, such as the 4-methyl- or 4-ethyl- or 4-benzylhexahydro-1H-1,4-diazepin-1-yl group; or the 1,2,3,6-tetrahydropyrid-1-yl group.

The cyclization of compounds of formula II (to obtain the pyrazolobenzodiazepinones according to the invention of formula I in which $R^3$ denotes a hydrogen atom) is effected by conventional processes. Thus, the cyclization of carboxylic acids II (X=—OH) is effected, for example, by warming, preferably in the presence of a proton donor, to temperatures between 90° C. and 220° C., preferably 120° to 160° C., in the absence, or preferably in the presence, of an inert solvent. Possible proton donors are inorganic acids and organic acids, for example hydrogen halide acids, such as hydrochloric acid, phosphoric acid, p-toluenesulfonic acid or acetic acid. Suitable inert solvents are aqueous or non-aqueous media, such as toluene, xylene, chlorobenzene, o-dichlorobenzene, trichlorobenzenes or diphenyl ether. The elimination of water in a nonaqueous reaction medium is, if appropriate, facilitated with the aid of a water separator or by adding a drying agent, for example a molecular sieve.

The cyclization is alternatively effected with the aid of a chemical condensing agent by means of which reactive acid derivatives are formed intermediately as intermediate stages, such as acid halides, mixed acid anhydrides, O-acylureas or activated esters. Examples of chemical condensing agents are dicyclohexylcarbodiimide, chloroformic acid ethyl ester, chloroformic acid isopropyl ester, chloroacetonitrile or phosphorus oxychloride. This cyclization reaction is carried out in an inert solvent, for example tetrahydrofuran, dioxan, dimethylformamide or N-methylpyrrolidone, at temperatures from —10° C. to 120° C., preferably from 0° C. to 60° C., if appropriate in the presence of an auxiliary base, for example an anhydrous alkali-metal carbonate, triethylamine or pyridine.

In the case of the carboxylic acid esters II (X=—O—$R^9$) or the carboxamides II [X=—N($R^{10}$)$R^{11}$], the cyclization is carried out at temperatures between 0° and 200° C., preferably between 20° and 160° C., in the absence, or in the presence, of an inert solvent, if appropriate in the presence of a basic catalyst or preferably an acid catalyst. The reaction times are between 15 minutes and 4 hours. Examples of possible solvents are alcohols, such as ethanol or glycol; ethers, such as dioxan or diphenyl ether; aromatic hydrocarbons, such as toluene, xylene or o-dichlorobenzene; or dimethylsulfoxide. Catalysts are basic catalysts, such as alkali-metal alkanolates, for examples sodium ethylate or potassium tert.-butanolate, or preferably sodium hydride; or acid catalysts, such as organic or inorganic acids, for example acetic acid, chloroacetic acid, p-toluenesulfonic acid, o-chlorobenzoic acid, p-toluic acid, nicotinic acid, trifluoroacetic acid, fumaric acid, hydrochloric acid, phosphoric acid or potassium bisulfate or, preferably, benzoic acid, up to 2 to 3 mols of acid catalyst being employed per mol of starting compound. When an aminoester of formula II (X=—O—$R^9$) is prepared by reducing a nitro compound of formula VI under suitable reaction conditions, the tricyclic compound of formula I ($R^3$=—H) is directly formed. The cyclization is preferably carried out using an amino compound II [X=—N($R^{10}$)$R^{11}$].

The substitution which follows is carried out by known methods.

In order to prepare the pyrazolobenzodiazepinones of formula I in which $R^3$ denotes —CO—A—Hal, the resulting reaction product of formula I (wherein $R^1$ and $R^2$ have their previously-ascribed meanings and $R^3$ denotes a hydrogen atom) or an acid-addition salt thereof, is reacted with a compound of the formula Hal-A-CO-Hal' (III) or of the formula [Hal-A-CO]$_2$O (IV), wherein Hal' has one of the meanings of Hal, and A and Hal have their previously-noted meanings. This reaction is carried out without a solvent or, preferably, in an inert solvent at room or elevated temperature, not higher than the boiling point of the solvent, if appropriate in the presence of an auxiliary base and/or an acylation catalyst.

The acid halides III are preferred over the acid anhydrides IV. Chloroacetyl chloride is preferred as the acid halide III, and chloroacetic anhydride is preferred as the acid anhydride IV. Examples of suitable solvents are aromatic hydrocarbons, such as toluene, xylene or chlorobenzene; open-chain or cyclic ethers, such as diisopropyl ether or dioxane; chlorinated hydrocarbons, such as dichloroethane, and other solvents, such as pyridine, acetonitrile or dimethylformamide.

Examples of auxiliary bases are tertiary organic bases, such as triethylamine and ethyldiisopropylamine, or pyridine; or inorganic bases, such as anhydrous alkali-metal carbonates or bicarbonates, alkaline-earth-metal carbonates or bicarbonates or alkaline-earth-metal oxides. Examples of acylation catalysts are imidazole, pyridine or 4-dimethylaminopyridine.

The process for preparing intermediate products of formula I is, therefore, characterized by cyclizing an anilinopyrazole derivative of formula II and, if appropriate, subsequently substituting the obtained product by reaction with a compound of formula III or of formula IV and/or converting the resulting base or its acid-addition salt from one to the other. Corresponding starting materials are employed in the preparation of intermediate products I*.

In order to prepare the pyrazolobenzodiazepinones of formula I [in which $R^1$ and $R^2$ have their noted meanings and $R^3$ denotes —CO—A—N($R^5$)$R^6$], the resulting reaction product of formula I wherein $R^3$ denotes —CO—A—Hal is reacted with a secondary amine of the formula HN($R^5$)$R^6$ (V) [$R^5$, $R^6$, A and Hal having their previously-ascribed meanings].

The reaction is carried out in an inert solvent at temperatures between 0° and the boiling point of the solvent, either using at least 2 mols of a secondary amine V or using from 1 to 2 mols of a secondary amine V and an auxiliary base. Examples of suitable solvents are chlorinated hydrocarbons, such as methylene chloride, chloroform or dichloroethane; open-chain or cyclic ethers, such as diethyl ether, tetrahydrofuran or dioxane; aromatic hydrocarbons, such as benzene, toluene, xylene, chlorobenzene or pyridine; alcohols, such as ethanol or isopropanol; and ketones, such as acetone; acetonitrile or dimethylformamide. Examples of auxiliary bases are tertiary organic bases, such as triethylamine, N-methylpiperidine, diethylaniline or pyridine; or inorganic bases, such as alkali-metal carbonates or bicarbonates, alkaline-earth-metal carbonates or bicarbonates or alkaline-earth-metal hydroxides or oxides. In some cases, the reaction is accelerated by incorporating an alkali-metal iodide in the reaction mixture. The reaction time is from 15 minutes to 80 hours, depending on the quantity and nature of the amine V employed. When starting compounds in which A represents an alkylene group with from 2 to 5 carbon atoms are reacted, the reaction can also proceed with the elimination of H-Hal; the alkenyl compound (which is formed as an intermediate and can, if desired, be isolated) reacts with the secondary amine V to yield the same end product.

The process for the preparation of the pharmacologically-active pyrazolobenzodiazepinones of formula I is, therefore, characterized by reacting a compound of formula I (wherein $R^3$ denotes —CO—A—Hal) with a compound of formula V and, if appropriate, subsequently converting the resulting base into a pharmacologically-acceptable acid-addition salt or converting a resulting acid-addition salt into the corresponding free base or into another and pharmacologically-acceptable acid-addition salt.

Acid-addition salts are obtained by dissolving the obtained free base in a suitable solvent, for example water, acetone, an alkanol, such as ethanol or isopropanol, or an open-chain or cyclic ether, such as diethyl ether or tetrahydrofuran, which contains the desired acid or to which the desired acid is subsequently added. The salts are obtained by filtering the mixture and causing precipitation by means of a non-solvent for the acid-addition salt or by evaporating the solvent. By conversion into the corresponding free base and further reaction with another acid, salts are converted into other salts, for example pharmacologically-acceptable acid-addition salts.

Resulting salts are converted (for example, by being rendered alkaline with aqueous sodium hydroxide or potassium hydroxide) into the free base, which is then isolated by suitable measures, for example solvent extraction with a solvent, such as chloroform, diethyl ether or toluene, which is not miscible with water.

The preparation of the starting compounds of formula II is effected by reducing nitro compounds of the formula

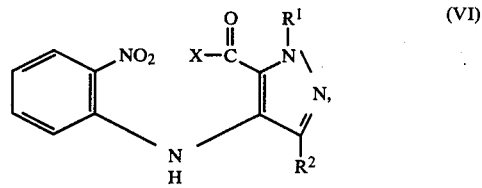

(VI)

wherein $R^1$, $R^2$ and X have their previously-ascribed meanings.

The reduction of the nitro compounds is effected by customary methods, for example by means of sodium dithionite, hydrazine hydrate and Raney nickel or by means of hydrogen in the presence of a catalyst, such as Raney nickel or palladium-on-charcoal, at normal pressure or under elevated pressure, at room temperature or at elevated temperature, in a customary solvent, such as water, an alcohol, an ether or glacial acetic acid, and, if appropriate, in the presence of mineral acid, such as hydrochloric acid or perchloric acid.

The preparation of the anilinopyrazolecarboxylic acids of formula II (X=—OH) is alternatively effected from the corresponding acid derivatives of formula II [X=—O—$R^9$ or —N($R^{10}$)$R^{11}$] by hydrolysis in an acid or alkaline medium in accordance with established known methods.

The preparation of starting compounds of formula VI (X=—OH) is effected by hydrolyzing esters or amides of formula VI [X=—O—$R^9$ or —N($R^{10}$)$R^{11}$, respectively] in an acid or alkaline medium under customary conditions. Conversely, the esters or amides of formula VI [X=—O—$R^9$ or —N($R^{10}$)$R^{11}$, respectively] are obtained from acids of formula VI (X=—OH) by customary methods, for example by converting the acid into an acid halide and reacting the latter with R⁹—OH, for example, with a corresponding alcohol or phenol or with the corresponding alcoholate or phenolate, or with an amine HN(R¹⁰)R¹¹.

The esters of formula VI, in particular the alkyl esters, or the amides of formula VI [X=—O—R⁹ or —N(R¹⁰)R¹¹, respectively] are obtained by reacting aminopyrazolecarboxylic acid esters of formula VII or aminopyrazolecarboxylic acid amides of formula VII [X=—O—R⁹ or —N(R¹⁰)R¹¹, respectively] with an o-halonitrobenzene (for example with o-bromonitrobenzene, with the addition of copper catalysts, or with o-chloronitrobenzene or, preferably, o-fluoronitrobenzene or a mixture of o-chloronitrobenzene and fluoronitrobenzene, such as is formed in the reaction of o-chloronitrobenzene with potassium fluoride, with the addition of a deprotonating agent, for example sodium hydride, potassium carbonate or a tertiary amine).

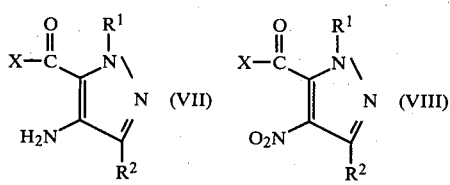

The compounds of formula VII are prepared by conventionally reducing compounds of formula VIII. Compounds of formula VIII are prepared from corresponding non-nitrated pyrazolecarboxylic acids, which are known from the literature or are prepared by analogous methods, by nitrating the latter and optionally converting them into esters or amides. Unsubstituted carboxamides of formula VIII are obtained by hydrolyzing corresponding nitriles, which are prepared from corresponding 5-halogenopyrazoles and cyanides by processes which are known from the literature. Preparative processes for starting materials are described, for example, in: H. A. De Wald et al., J. Med. Chem., 16, 1,346 (1973); U.S. Pat. No. 3,657,271; U.S. Pat. No. 3,939,161; C. Musante, Gazz. chim. ital., 75, 121–136 (1945); C. A. Rojahn, Ber. Dt. Chem. Ges., 59, 607–611 (1926); L. B. Townsend et al., J. Org. Chem., 39, 2,023–2,027 (1974); German Offenlegungsschrift No. 2,250,316; and U.S. Pat. No. 3,553,209.

In order to prepare compounds I* or I**, corresponding starting compounds II*, II**, III*, III**, IV*, IV and V are employed.

The examples which follow serve to illustrate the invention in greater detail. In their text "mp" denotes "melting point"; "bp" denotes "boiling point"; and "dec." represents "with decomposition".

EXAMPLE 1

3.5 g of 4-chloroacetyl-1,3-dimethyl-1,4,9,10-tetrahydropyrazolo[4,3-b][1,5]benzodiazepin-10-one, 8.1 g of N-methylpiperazine and 50 ml of toluene are stirred at 80° C. for 2 hours. 60 ml of dilute sodium bicarbonate solution are added to the mixture, the layers are separated and the aqueous phase is extracted by shaking it with toluene several times more before concentrating it to dryness in vacuo. The residue is stirred with 100 ml of isopropanol and is filtered; the filtrate is concentrated in vacuo. The residue (4.0 g) is purified by stirring it with diethyl ether and by recrystallizing it from toluene, which yields 2.2 g of 1,3-dimethyl-4-[(4-methylpiperazin-1-yl)acetyl]-1,4,9,10-tetrahydropyrazolo[4,3-b][1,5]benzodiazepin-10-one, mp 186° to 188° C.; succinate, mp 172° to 174° C.

EXAMPLE 2

15.0 g of 4-chloroacetyl-1,3-dimethyl-1,4,9,10-tetrahydropyrazolo[4,3-b][1,5]benzodiazepin-10-one, 21 g of N-methylpiperazine and 70 ml of dioxane are stirred at 80° C. for 1 hour (complete reaction being already indicated by a thin layer chromatogram after 20 minutes), and the thus-obtained solution is concentrated to dryness in vacuo. 150 ml of isopropanol and 40 ml of water are added to the residue, 25 ml of concentrated hydrochloric acid are then added dropwise and the resulting mixture is cooled in an icebath to obtain 1,3-dimethyl-4-[(4-methylpiperazin-1-yl)acetyl]-1,4,9,10-tetrahydropyrazolo[4,3-b][1,5]benzodiazepin-10-one dihydrochloride mixed with N-methylpiperazine hydrochloride. The hydrochlorides are dissolved in water and chloroform, the pH is adjusted to 8.2 with 2 N sodium hydroxide solution, the aqueous phase is exhaustively extracted by shaking it with chloroform and the organic solution is dried and concentrated to dryness in vacuo. This yields 17.6 g of 1,3-dimethyl-4-[(4-methylpiperazin-1-yl)acetyl]-1,4,9,10-tetrahydropyrazolo[4,3-b][1,5]benzodiazepin-10-one, mp 186° to 188° C. (from toluene); dihydrochloride, mp 222° to 224° C. (dec.); hemi fumarate, mp 257° to 258° C. (dec.).

1,3-Dimethyl-4-(morpholinoacetyl)-1,4,9,10-tetrahydropyrazolo[4,3-b][1,5]benzodiazepin-10-one (mp 201° to 203° C.), 4-[(4-benzylpiperazin-1-yl)acetyl]-1,3-dimethyl-1,4,9,10-tetrahydropyrazolo[4,3-b][1,5]benzodiazepin-10-one (mp 215° to 218° C.), 4-[(4-ethylpiperazin-1-yl)acetyl]-1,3-dimethyl-1,4,9,10-tetrahydropyrazolo[4,3-b][1,5]-benzodiazepin-10-one, 4-[(2,4-dimethylpiperazin-1-yl)acetyl]-1,3-dimethyl-1,4,9,10-tetrahydropyrazolo[4,3-b][1,5]benzodiazepin-10-one, 4-{[N-(2-dimethylaminoethyl)-N-methylamino]acetyl}-1,3-dimethyl-1,4,9,10-tetrahydropyrazolo[4,3-b][1,5]benzodiazepin-10-one (mp 84° to 86° C.), 4-{[N-(2-diethylaminoethyl)-N-ethylamino]acetyl}-1,3-dimethyl-1,4,9,10-tetrahydropyrazolo[4,3-b][1,5]benzodiazepin-10-one (mp 139.5° to 141° C.), 4-{[N-(2-dimethylaminoethyl)-N-ethylamino]acetyl}-1,3-dimethyl-1,4,9,10-tetrahydropyrazolo[4,3-b][1,5]benzodiazepin-10-one (mp 93° to 95.5° C.) and 4-[(hexahydro-4-methyl-1H-1,4-diazepin-1-yl)acetyl]-1,3-dimethyl-1,4,9,10-tetrahydropyrazolo[4,3-b][1,5]benzodiazepin-10-one are obtained analogously by reacting 4-chloroacetyl-1,3-dimethyl-1,4,9,10-tetrahydropyrazolo[4,3-b][1,5]benzodiazepin-10-one with corresponding amounts (instead of with N-methylpiperazine) of morpholine, N-benzylpiperazine, N-ethylpiperazine, 1,3-dimethylpiperazine, N,N,N'-trimethylethylenediamine, N,N,N'-triethylethylenediamine, N'-ethyl-N,N-dimethylethylenediamine and hexahydro-1-methyl-1H-1,4-diazepine, respectively.

EXAMPLE 3

2.0 g of 4-chloroacetyl-1,3-dimethyl-1,4,9,10-tetrahydropyrazolo[4,3-b][1,5]benzodiazepin-10-one, 0.55 g of pyrrolidine, 0.85 g of ground sodium carbonate and 15 ml of absolute ethanol are heated at the boil for 2 hours; the hot solution is then filtered and concentrated in vacuo. The thus-obtained residue is dissolved in ethylene chloride, and the resulting organic solution is washed at pH 7 with water and concentrated to yield 2.05 g of 1,3-dimethyl-4-(pyrrolidinoacetyl)-1,4,9,10-tetrahydropyrazolo[4,3-b][1,5]benzodiazepin-10-one, mp 114° to 116° C. (from toluene).

EXAMPLE 4

2 g of 4-chloroacetyl-1,3-dimethyl-1,4,9,10-tetrahydropyrazolo[4,3-b][1,5]benzodiazepin-10-one, 3.7 g of piperidine and 15 ml of dioxane are stirred at 80° C. for 1 hour; the resulting mixture is concentrated in vacuo, and the produced residue is recrystallized from isopropanol/water and toluene/petroleum ether. This yields 2.0 g of 1,3-dimethyl-4-(piperidinoacetyl)-1,4,9,10-tetrahydropyrazolo[4,3-b][1,5]benzodiazepin-10-one, mp 156° to 158° C.

1,3-Dimethyl-4-(pyrrolidinoacetyl)-1,4,9,10-tetrahydropyrazolo[4,3-b][1,5]benzodiazepin-10-one (mp 114° to 116° C.),
4-(diethylaminoacetyl)-1,3-dimethyl-1,4,9,10-tetrahydropyrazolo[4,3-b][1,5]benzodiazepin-10-one (mp 142.5° to 144° C.),
4-[di-(n-propyl)aminoacetyl]-1,3-dimethyl-1,4,9,10-tetrahydropyrazolo[4,3-b][1,5]benzodiazepin-10-one,
4-[di-(n-butyl)aminoacetyl]-1,3-dimethyl-1,4,9,10-tetrahydropyrazolo[4,3-b][1,5]benzodiazepin-10-one,
4-[N-ethyl-N-(n-butyl)aminoacetyl]-1,3-dimethyl-1,4,9,10-tetrahydropyrazolo[4,3-b][1,5]benzodiazepin-10-one,
4-(diallylaminoacetyl)-1,3-dimethyl-1,4,9,10-tetrahydropyrazolo[4,3-b][1,5]benzodiazepin-10-one,
4-[(hexahydroazepin-1-yl)acetyl]-1,3-dimethyl-1,4,9,10-tetrahydropyrazolo[4,3-b][1,5]benzodiazepin-10-one and
1,3-dimethyl-4-[{N-methyl-N-(n-butyl)amino}acetyl]-1,4,9,10-tetrahydropyrazolo[4,3-b][1,5]benzodiazepin-10-one
are obtained analogously by reacting 4-chloroacetyl-1,3-dimethyl-1,4,9,10-tetrahydropyrazolo[4,3-b][1,5]benzodiazepin-10-one with corresponding amounts (instead of with piperidine) of pyrrolidine, diethylamine, di-(n-propyl)amine, di-(n-butyl)amine, N-ethyl-N-(n-butyl)amine, diallylamine, hexahydroazepine and N-methyl-N-(n-butyl)amine, respectively.

EXAMPLE 5

2.0 g of 4-chloroacetyl-1,3-dimethyl-1,4,9,10-tetrahydropyrazolo[4,3-b][1,5]benzodiazepin-10-one, 5.6 ml of 40% strength aqueous dimethylamine solution and 10 ml of methylene chloride are stirred at 35° C. for 2 hours; 0.35 g of sodium carbonate are added, and the obtained mixture is concentrated to dryness in vacuo. A little water is added thereto, the resulting solution is extracted repeatedly by shaking it with chloroform, and the thus-prepared organic solution is dried with sodium sulfate and concentrated to dryness. This yields 1.9 g of 4-(dimethylaminoacetyl)-1,3-dimethyl-1,4,9,10-tetrahydropyrazolo[4,3-b][1,5]benzodiazepin-10-one, mp 178° to 179° C. (from toluene).

EXAMPLE 6

2.0 g of 4-chloroacetyl-1,3-dimethyl-1,4,9,10-tetrahydropyrazolo[4,3-b][1,5]benzodiazepin-10-one, 9 ml of diisopropylamine, 100 mg of potassium iodide and 15 ml of dioxane are stirred under reflux for 70 hours and the solution is concentrated in vacuo. Water and dilute hydrochloric acid are added to give a pH value of 4; the resulting solution is extracted by shaking it with ethyl methyl ketone and is clarified with active charcoal. Dilute sodium hydroxide solution is used to precipitate (from the aqueous solution at pH 9.5, while cooling with ice) colorless crystals which are recrystallized from 1:1 petroleum ether (bp 50° to 70° C.)/ethyl acetate. This yields 1.8 g of 4-(diisopropylaminoacetyl)-1,3-dimethyl-1,4,9,10-tetrahydropyrazolo[4,3-b][1,5]benzodiazepin-10-one, mp 154° to 156° C.

4-[N-(n-butyl)-N-(tert.-butyl)aminoacetyl]-1,3-dimethyl-1,4,9,10-tetrahydropyrazolo[4,3-b][1,5]benzodiazepin-10-one,
4-(diisobutylaminoacetyl)-1,3-dimethyl-1,4,9,10-tetrahydropyrazolo[4,3-b][1,5]benzodiazepin-10-one,
4-[di-(sec.-butyl)aminoacetyl]-1,3-dimethyl-1,4,9,10-tetrahydropyrazolo[4,3-b][1,5]benzodiazepin-10-one,
1,3-dimethyl-4-[N-methyl-N-(tert.-butyl)aminoacetyl]-1,4,9,10-tetrahydropyrazolo[4,3-b][1,5]benzodiazepin-10-one and
1,3-dimethyl-4-[N-methyl-N-(sec.-butyl)aminoacetyl]-1,4,9,10-tetrahydropyrazolo[4,3-b][1,5]benzodiazepin-10-one
are obtained analogously by reacting 4-chloroacetyl-1,3-dimethyl-1,4,9,10-tetrahydropyrazolo[4,3-b][1,5]benzodiazepin-10-one with corresponding amounts (instead of with diisopropylamine) of N-(n-butyl)-N-(tert.-butyl)amine, diisobutylamine, di-(sec.-butyl)amine, N-methyl-N-(tert.-butyl)amine and N-methyl-N-(sec.-butyl)amine, respectively.

EXAMPLE 7

3.5 g of 4-chloroacetyl-1-ethyl-3-methyl-1,4,9,10-tetrahydropyrazolo[4,3-b][1,5]benzodiazepin-10-one, 4.4 g of N-methylpiperazine and 20 ml of dioxane are reacted in accordance with Example 2. This yields 3.0 g of 1-ethyl-3-methyl-4-[(4-methylpiperazin-1-yl)acetyl]-1,4,9,10-tetrahydropyrazolo[4,3-b][1,5]benzodiazepin-10-one, mp 145° to 146° C.

1-Ethyl-4-[(4-ethylpiperazin-1-yl)acetyl]-3-methyl-1,4,9,10-tetrahydropyrazolo[4,3-b][1,5]benzodiazepin-10-one and 4-[(2,4-dimethylpiperazin-1-yl)acetyl]-1-ethyl-3-methyl-1,4,9,10-tetrahydropyrazolo[4,3-b][1,5]benzodiazepin-10-one are obtained analogously by reacting 4-chloroacetyl-1-ethyl-3-methyl-1,4,9,10-tetrahydropyrazolo[4,3-b][1,5]benzodiazepin-10-one with corresponding amounts of 1-ethylpiperazine and 1,3-dimethylpiperazine, respectively, instead of with N-methylpiperazine.

EXAMPLE 8

4-[(4-Ethylpiperazin-1-yl)acetyl]-1-isopropyl-3-methyl-1,4,9,10-tetrahydropyrazolo[4,3-b][1,5]benzodiazepin-10-one,
3-ethyl-4-[(4-ethylpiperazin-1-yl)acetyl]-1-methyl-1,4,9,10-tetrahydropyrazolo[4,3-b][1,5]benzodiazepin-10-one,
4-[(4-ethylpiperazin-1-yl)acetyl]-3-isopropyl-1-methyl-1,4,9,10-tetrahydropyrazolo[4,3-b][1,5]benzodiazepin-10-one,
4-[(4-ethylpiperazin-1-yl)acetyl]-1-methyl-1,4,9,10-tetrahydropyrazolo[4,3-b][1,5]benzodiazepin-10-one,
1-ethyl-4-[(4-ethylpiperazin-1-yl)acetyl]-1,4,9,10-tetrahydropyrazolo[4,3-b][1,5]benzodiazepin-10-one,
4-[(4-ethylpiperazin-1-yl)acetyl]-1-isopropyl-1,4,9,10-tetrahydropyrazolo[4,3-b][1,5]benzodiazepin-10-one, 4-[3-(4-ethylpiperazin-1-yl)propionyl]-1,3-dimethyl-1,4,9,10-tetrahydropyrazolo[4,3-b][1,5]benzodiazepin-10-one,
4-[2-(4-ethylpiperazin-1-yl)propionyl]-1,3-dimethyl-1,4,9,10-tetrahydropyrazolo[4,3-b][1,5]benzodiazepin-10-one,
4-[(2,4-dimethylpiperazin-1-yl)acetyl]-1-isopropyl-3-methyl-1,4,9,10-tetrahydropyrazolo[4,3-b][1,5]benzodiazepin-10-one,
4-[(2,4-dimethylpiperazin-1-yl)acetyl]-3-ethyl-1-methyl-1,4,9,10-tetrahydropyrazolo[4,3-b][1,5]benzodiazepin-10-one,
4-[(2,4-dimethylpiperazin-1-yl)acetyl]-3-isopropyl-1-methyl-1,4,9,10-tetrahydropyrazolo[4,3-b][1,5]benzodiazepin-10-one,
4-[(2,4-dimethylpiperazin-1-yl)acetyl]-1-methyl-1,4,9,10-tetrahydropyrazolo[4,3-b][1,5]benzodiazepin-10-one,
4-[(2,4-dimethylpiperazin-1-yl)acetyl]-1-ethyl-1,4,9,10-tetrahydropyrazolo[4,3-b][1,5]benzodiazepin-10-one,
4-[(2,4-dimethylpiperazin-1-yl)acetyl]-1-isopropyl-1,4,9,10-tetrahydropyrazolo[4,3-b][1,5]benzodiazepin-10-one,
4-[3-(2,4-dimethylpiperazin-1-yl)propionyl]-1,3-dimethyl-1,4,9,10-tetrahydropyrazolo[4,3-b][1,5]benzodiazepin-10-one and
4-[2-(2,4-dimethylpiperazin-1-yl)propionyl]-1,3-dimethyl-1,4,9,10-tetrahydropyrazolo[4,3-b][1,5]benzodiazepin-10-one
are obtained analogously to Example 2 by reacting
4-chloroacetyl-1-isopropyl-3-methyl-1,4,9,10-tetrahydropyrazolo[4,3-b][1,5]benzodiazepin-10-one,
4-chloroacetyl-3-ethyl-1-methyl-1,4,9,10-tetrahydropyrazolo[4,3-b][1,5]benzodiazepin-10-one,
4-chloroacetyl-3-isopropyl-1-methyl-1,4,9,10-tetrahydropyrazolo[4,3-b][1,5]benzodiazepin-10-one,
4-chloroacetyl-1-methyl-1,4,9,10-tetrahydropyrazolo[4,3-b][1,5]benzodiazepin-10-one,
4-chloroacetyl-1-ethyl-1,4,9,10-tetrahydropyrazolo[4,3-b][1,5]benzodiazepin-10-one,
4-chloroacetyl-1-isopropyl-1,4,9,10-tetrahydropyrazolo[4,3-b][1,5]benzodiazepin-10-one,
4-(3-chloropropionyl)-1,3-dimethyl-1,4,9,10-tetrahydropyrazolo[4,3-b][1,5]benzodiazepin-10-one and, respectively,
4-(2-chloropropionyl)-1,3-dimethyl-1,4,9,10-tetrahydropyrazolo[4,3-b][1,5-benzodiazepin-10-one
with corresponding amounts of 1-ethylpiperazine and 1,3-dimethylpiperazine (instead of with N-methylpiperazine), respectively.

EXAMPLE 9

1-Isopropyl-3-methyl-4-[(4-methylpiperazin-1-yl)acetyl]-1,4,9,10-tetrahydropyrazolo[4,3-b][1,5]benzodiazepin-10-one,
3-isopropyl-1-methyl-4-[(4-methylpiperazin-1-yl)acetyl]-1,4,9,10-tetrahydropyrazolo[4,3-b][1,5]benzodiazepin-10-one,
3-ethyl-1-methyl-4-[(4-methylpiperazin-1-yl)acetyl]-1,4,9,10-tetrahydropyrazolo[4,3-b][1,5]benzodiazepin-10-one (mp 214° to 216° C.),
1-methyl-4-[(4-methylpiperazin-1-yl)acetyl]-1,4,9,10-tetrahydropyrazolo[4,3-b][1,5]benzodiazepin-10-one (mp 198,5° to 200,5° C.),
1-ethyl-4-[(4-methylpiperazin-1-yl)acetyl]-1,4,9,10-tetrahydropyrazolo[4,3-b][1,5]benzodiazepin-10-one,
1-isopropyl-4-[(4-methylpiperazin-1-yl)acetyl]-1,4,9,10-tetrahydropyrazolo[4,3-b][1,5]benzodiazepin-10-one,
1,3-dimethyl-4-[3-(4-methylpiperazin-1-yl)propionyl]-1,4,9,10-tetrahydropyrazolo[4,3-b][1,5]benzodiazepin-10-one (mp 105° to 110° C.),
3-ethyl-1-methyl-4-[3-(4-methylpiperazin-1-yl)propionyl]-1,4,9,10-tetrahydropyrazolo[4,3-b][1,5]benzodiazepin-10-one,
3-isopropyl-1-methyl-4-[3-(4-methylpiperazin-1-yl)propionyl]-1,4,9,10-tetrahydropyrazolo[4,3-b][1,5]benzodiazepin-10-one,
1-methyl-4-[3-(4-methylpiperazin-1-yl)propionyl]-1,4,9,10-tetrahydropyrazolo[4,3-b][1,5]benzodiazepin-10-one,
1-ethyl-4-[3-(4-methylpiperazin-1-yl)propionyl]-1,4,9,10-tetrahydropyrazolo[4,3-b][1,5]benzodiazepin-10-one,
1-isopropyl-4-[3-(4-methylpiperazin-1-yl)propionyl]-1,4,9,10-tetrahydropyrazolo[4,3-b[1,5]benzodiazepin-10-one,
1,3-dimethyl-4-[2-(4-methylpiperazin-1-yl)propionyl]-1,4,9,10-tetrahydropyrazolo[4,3-b][1,5]benzodiazepin-10-one,
3-ethyl-1-methyl-4-[2-(4-methylpiperazin-1-yl)propionyl]-1,4,9,10-tetrahydropyrazolo[4,3-b][1,5]benzodiazepin-10-one,
3-isopropyl-1-methyl-4-[2-(4-methylpiperazin-1-yl)propionyl]-1,4,9,10-tetrahydropyrazolo[4,3-b][1,5]benzodiazepin-10-one,
1-methyl-4-[2-(4-methylpiperazin-1-yl)propionyl]-1,4,9,10-tetrahydropyrazolo[4,3-b][1,5]benzodiazepin-10-one,
1-ethyl-4-[2-(4-methylpiperazin-1-yl)propionyl]-1,4,9,10-tetrahydropyrazolo[4,3-b][1,5 benzodiazepin-10-one,
1-isopropyl-4-[2-(4-methylpiperazin-1-yl)propionyl]-1,4,9,10-tetrahydropyrazolo[4,3-b][1,5]benzodiazepin-10-one,
1,3-dimethyl-4-[4-(4-methylpiperazin-1-yl)butyryl]-1,4,9,10-tetrahydropyrazolo[4,3-b][1,5]benzodiazepin-10-one,
1-methyl-4-[4-(4-methylpiperazin-1-yl)butyryl]-1,4,9,10-tetrahydropyrazolo[4,3-b][1,5]benzodiazepin-10-one,
1-ethyl-4-[4-(4-methylpiperazin-1-yl)butyryl]-1,4,9,10-tetrahydropyrazolo[4,3-b][1,5]benzodiazepin-10-one,
1,3-dimethyl-4-[5-(4-methylpiperazin-1-yl)valeryl]-1,4,9,10-tetrahydropyrazolo[4,3-b][1,5]benzodiazepin-10-one,
1-methyl-4-[5-(4-methylpiperazin-1-yl)valeryl]-1,4,9,10-tetrahydropyrazolo[4,3-b][1,5]benzodiazepin-10-one and
1-ethyl-4-[5-(4-methylpiperazin-1-yl)valeryl]-1,4,9,10-tetrahydropyrazolo[4,3-b][1,5]benzodiazepin-10-one
are obtained analogously to Example 2 by reacting
4-chloroacetyl-1-isopropyl-3-methyl-1,4,9,10-tetrahydropyrazolo[4,3-b][1,5]benzodiazepin-10-one,
4-chloroacetyl-3-isopropyl-1-methyl-1,4,9,10-tetrahydropyrazolo[4,3-b][1,5]benzodiazepin-10-one,
4-chloroacetyl-3-ethyl-1-methyl-1,4,9,10-tetrahydropyrazolo[4,3-b][1,5]benzodiazepin-10-one,
4-chloroacetyl-1-methyl-1,4,9,10-tetrahydropyrazolo[4,3-b][1,5]benzodiazepin-10-one,
4-chloroacetyl-1-ethyl-1,4,9,10-tetrahydropyrazolo[4,3-b][1,5]benzodiazepin-10-one,
4-chloroacetyl-1-isopropyl-1,4,9,10-tetrahydropyrazolo[4,3-b][1,5]benzodiazepin-10-one,
4-(3-chloropropionyl)-1,3-dimethyl-1,4,9,10-tetrahydropyrazolo[4,3-b][1,5]benzodiazepin-10-one, 4-(3-chloropropionyl)-3-ethyl-1-methyl-1,4,9,10-tetrahydropyrazolo[4,3-b][1,5]benzodiazepin-10-one,
4-(3-chloropropionyl)-3-isopropyl-1-methyl-1,4,9,10-tetrahydropyrazolo[4,3-b][1,5]benzodiazepin-10-one,
4-(3-chloropropionyl)-1-methyl-1,4,9,10-tetrahydropyrazolo[4,3-b][1,5]benzodiazepin-10-one,
4-(3-chloropropionyl)-1-ethyl-1,4,9,10-tetrahydropyrazolo[4,3-b][1,5]benzodiazepin-10-one,
4-(3-chloropropionyl-1-isopropyl-1,4,9,10-tetrahydropyrazolo[4,3-b][1,5]benzodiazepin-10-one,
4-(2-chloropropionyl)-1,3-dimethyl-1,4,9,10-tetrahydropyrazolo[4,3-b][1,5]benzodiazepin-10-one,
4-(2-chloropropionyl)-3-ethyl-1-methyl-1,4,9,10-tetrahydropyrazolo[4,3-b][1,5]benzodiazepin-10-one,
4-(2-chloropropionyl)-3-isopropyl-1-methyl-1,4,9,10-tetrahydropyrazolo[4,3-b][1,5]benzodiazepin-10-one,
4-(2-chloropropionyl)-1-methyl-1,4,9,10-tetrahydropyrazolo[4,3-b][1,5]benzodiazepin-10-one,
4-(2-chloropropionyl)-1-ethyl-1,4,9,10-tetrahydropyrazolo[4,3-b][1,5]benzodiazepin-10-one,
4-(2-chloropropionyl)-1-isopropyl-1,4,9,10-tetrahydropyrazolo[4,3-b][1,5]benzodiazepin-10-one,
4-(4-chlorobutyryl)-1,3-dimethyl-1,4,9,10-tetrahydropyrazolo[4,3-b][1,5]benzodiazepin-10-one,
4-(4-chlorobutyryl)-1-methyl-1,4,9,10-tetrahydropyrazolo[4,3-b][1,5]benzodiazepin-10-one,
4-(4-chlorobutyryl)-1-ethyl-1,4,9,10-tetrahydropyrazolo[4,3-b][1,5]benzodiazepin-10-one,
4-(5-chlorovaleryl)-1,3-dimethyl-1,4,9,10-tetrahydropyrazolo[4,3-b][1,5]benzodiazepin-10-one,
4-(5-chlorovaleryl)-1-methyl-1,4,9,10-tetrahydropyrazolo[4,3-b][1,5]benzodiazepin-10-one and
4-(5-chlorovaleryl)-1-ethyl-1,4,9,10-tetrahydropyrazolo[4,3-b][1,5]benzodiazepin-10-one, respectively, with a corresponding amount of N-methylpiperazine.

EXAMPLE 10

4-(Dimethylaminoacetyl)-1-ethyl-3-methyl-1,4,9,10-tetrahydropyrazolo[4,3-b][1,5]benzodiazepin-10-one,
4-(dimethylaminoacetyl)-1-isopropyl-3-methyl-1,4,9,10-tetrahydropyrazolo[4,3-b][1,5]benzodiazepin-10-one,
4-(dimethylaminoacetyl)-3-ethyl-1-methyl-1,4,9,10-tetrahydropyrazolo[4,3-b][1,5]benzodiazepin-10-one,
4-(dimethylaminoacetyl)-3-isopropyl-1-methyl-1,4,9,10-tetrahydropyrazolo[4,3-b][1,5]benzodiazepin-10-one,
4-(dimethylaminoacetyl)-1-methyl-1,4,9,10-tetrahydropyrazolo[4,3-b][1,5]benzodiazepin-10-one,
4-(dimethylaminoacetyl)-1-ethyl-1,4,9,10-tetrahydropyrazolo[4,3-b][1,5]benzodiazepin-10-one,
4-(dimethylaminoacetyl)-1-isopropyl-1,4,9,10-tetrahydropyrazolo[4,3-b][1,5]benzodiazepin-10-one,
4-[3-(dimethylamino)propionyl]-1,3-dimethyl-1,4,9,10-tetrahydropyrazolo[4,3-b][1,5]benzodiazepin-10-one,
4-[2-(dimethylamino)propionyl]-1,3-dimethyl-1,4,9,10-tetrahydropyrazolo[4,3-b][1,5]benzodiazepin-10-one,
4-[4-(dimethylamino)butyryl]-1,3-dimethyl-1,4,9,10-tetrahydropyrazolo[4,3-b][1,5]benzodiazepin-10-one and
4-[5-(dimethylamino)valeryl]-1,3-dimethyl-1,4,9,10-tetrahydropyrazolo[4,3-b][1,5]benzodiazepin-10-one
are obtained analogously to Example 5 by reacting
4-chloroacetyl-1-ethyl-3-methyl-1,4,9,10-tetrahydropyrazolo[4,3-b][1,5]benzodiazepin-10-one,
4-chloroacetyl-1-isopropyl-3-methyl-1,4,9,10-tetrahydropyrazolo[4,3-b][1,5]benzodiazepin-10-one,
4-chloroacetyl-3-ethyl-1-methyl-1,4,9,10-tetrahydropyrazolo[4,3-b][1,5]benzodiazepin-10-one,
4-chloroacetyl-3-isopropyl-1-methyl-1,4,9,10-tetrahydropyrazolo[4,3-b][1,5]benzodiazepin-10-one,
4-chloroacetyl-1methyl-1,4,9,10-tetrahydropyrazolo[4,3-b][1,5]benzodiazepin-10-one,
4-chloroacetyl-1-ethyl-1,4,9,10-tetrahydropyrazolo[4,3-b][1,5]benzodiazepin-10-one,
4-chloroacetyl-1-isopropyl-1,4,9,10-tetrahydropyrazolo[4,3-b][1,5]benzodiazepin-10-one,
4-(3-chloropropionyl)-1,3-dimethyl-1,4,9,10-tetrahydropyrazolo[B 4,3-b][1,5]benzodiazepin-10-one,
4-(2-chloropropionyl)-1,3-dimethyl-1,4,9,10-tetrahydropyrazolo[4,3-b][1,5]benzodiazepin-10-one,
4-(4-chlorobutyryl)-1,3-dimethyl-1,4,9,10-tetrahydropyrazolo[4,3-b][1,5]benzodiazepin-10-one and
4(5-chlorovaleryl)-1,3-dimethyl-1,4,9,10-tetrahydropyrazolo[4,3-b][1,5]benzodiazepin-10-one,
respectively, with a corresponding amount of dimethylamine.

EXAMPLE 11

1-Ethyl-3-methyl-4-(pyrrolidinoacetyl)-1,4,9,10-tetrahydropyrazolo[4,3-b][1,5]benzodiazepin-10-one,
1-isopropyl-3-methyl-4-(pyrrolidinoacetyl)-1,4,9,10-tetrahydropyrazolo[4,3-b][1,5]benzodiazepin-10-one,
3-ethyl-1-methyl-4-(pyrrolidinoacetyl)-1,4,9,10-tetrahydropyrazolo[4,3-b][1,5]benzodiazepin-10-one,
3-isopropyl-1-methyl-4-(pyrrolidinoacetyl)-1,4,9,10-tetrahydropyrazolo[4,3-b][1,5]benzodiazepin-10-one,
1-methyl-4-(pyrrolidinoacetyl)-1,4,9,10-tetrahydropyrazolo[4,3-b][1,5]benzodiazepin-10-one (mp 197° to 199° C.),
1-ethyl-4-(pyrrolidinoacetyl)-1,4,9,10-tetrahydropyrazolo[4,3-b][1,5]benzodiazepin-10-one,
1-isopropyl-4-(pyrrolidinoacetyl)-1,4,9,10-tetrahydropyrazolo[4,3-b][1,5]benzodiazepin-10-one,
1,3-dimethyl-4-[3-(pyrrolidino)propionyl]-1,4,9,10-tetrahydropyrazolo[4,3-b][1,5]benzodiazepin-10-one,
1,3-dimethyl-4-[2-(pyrrolidino)propionyl]-1,4,9,10-tetrahydropyrazolo[4,3-b][1,5]benzodiazepin-10-one,
1,3-dimethyl-4-[4-(pyrrolidino)butyryl]-1,4,9,10-tetrahydropyrazolo[4,3-b][1,5]benzodiazepin-10-one and
1,3-dimethyl-4-[5-(pyrrolidino)valeryl]-1,4,9,10-tetrahydropyrazolo[4,3-b][1,5]benzodiazepin-10-one
are obtained analogously to Example 4 by reacting
4-chloroacetyl-1-ethyl-3-methyl-1,4,9,10-tetrahydropyrazolo[4,3-b][1,5]benzodiazepin-10-one,
4-chloroacetyl-1-isopropyl-3-methyl-1,4,9,10-tetrahydropyrazolo[4,3-b][1,5]benzodiazepin-10-one,
4-chloroacetyl-3-ethyl-1-methyl-1,4,9,10-tetrahydropyrazolo[4,3-b][1,5]benzodiazepin-10-one,
4-chloroacetyl-3-isopropyl-1-methyl-1,4,9,10-tetrahydropyrazolo[4,3-b][1,5]benzodiazepin-10-one,
4-chloroacetyl-1-methyl-1,4,9,10-tetrahydropyrazolo[4,3-b][1,5]benzodiazepin-10-one,
4-chloroacetyl-1-ethyl-1,4,9,10-tetrahydropyrazolo[4,3-b][1,5]benzodiazepin-10-one,
4-chloroacetyl-1-isopropyl-1,4,9,10-tetrahydropyrazolo[4,3-b][1,5]benzodiazepin-10-one,
4-(3-chloropropionyl)-1,3-dimethyl-1,4,9,10-tetrahydropyrazolo[4,3-b][1,5]benzodiazepin-10-one,
4-(2-chloropropionyl)-1,3-dimethyl-1,4,9,10-tetrahydropyrazolo[4,3-b][1,5]benzodiazepin-10-one,
4-(4-chlorobutyryl)-1,3-dimethyl-1,4,9,10-tetrahydropyrazolo[4,3-b][1,5]benzodiazepin-10-one and
4-(5-chlorovaleryl)-1,3-dimethyl-1,4,9,10-tetrahydropyrazolo[4,3-b][1,5]benzodiazepin-10-one, respectively, with a corresponding amount of pyrrolidine.

EXAMPLE 12

A solution of 2.1 g of chloroacetyl chloride in 10 ml of toluene is added dropwise over the course of 30 minutes at from 70° to 80° C. to 2.9 g of 1,3-dimethyl-1,4,9,10-tetrahydropyrazolo[4,3-b][1,5]benzodiazepin-10-one, 6 g of anhydrous potassium carbonate, 40 ml of dioxane and 20 ml of toluene, and the resulting mixture is stirred for a further 2 hours at this temperature. The mixture is then concentrated to dryness; the residue is extracted 3 times by boiling with 25 ml of chloroform each time, and the filtrate is concentrated to dryness. This yields 3.6 g of 4-chloroacetyl-1,3-dimethyl-1,4,9,10-tetrahydropyrazolo[4,3-b][1,5]benzodiazepin-10-one, mp 246° to 248° C. (dec.).

EXAMPLE 13

2 g of chloroacetyl chloride and 2 g of triethylamine are added dropwise at the same time over the course of 40 minutes to a boiling solution of 2.3 g of 1,3-dimethyl-1,4,9,10-tetrahydropyrazolo[4,3-b][1,5]benzodiazepin-10-one in 30 ml of absolute dioxane, and the mixture is stirred for a further 3 hours. It is then allowed to cool and is filtered; the filtrate is concentrated to dryness and chromatographed over a silica gel column by means of a 1:1 mixture of petroleum ether and ethyl acetate, and the product is recrystallized from toluene to yield 2.0 g of 4-chloroacetyl-1,3-dimethyl-1,4,9,10-tetrahydropyrazolo[4,3-b][1,5]benzodiazepin-10-one, mp 246° to 248° C. (dec.).

EXAMPLE 14

6.7 g of 1-ethyl-3-methyl-1,4,9,10-tetrahydropyazolo[4,3-b][1,5]benzodiazepin-10-one, 4.0 g of chloroacetyl chloride, 10 g of anhydrous potassium carbonate and 70 ml of dry dioxane are stirred under nitrogen for 1 hour at 80° C.; the mixture is filtered while still warm, and the precipitate of inorganic salts is extracted 3 times with warm chloroform. The organic filtrates are concentrated to dryness in vacuo; the residue is stirred with water and sodium bicarbonate solution at pH 6, washed with water and dried in vacuo at 50° C. This yields 8.7 g of 4-chloroacetyl-1-ethyl-3-methyl-1,4,9,10-tetrahydropyrazolo[4,3-b][1,5]benzodiazepin-10-one, mp 208° to 209.5° C.

4-Chloroacetyl-1,3-dimethyl-1,4,9,10-tetrahydropyrazolo[4,3-b][1,5]benzodiazepin-10-one (mp 246° to 248° C. with decomposition),
4-chloroacetyl-3-ethyl-1-methyl-1,4,9,10-tetrahydropyrazolo[4,3-b][1,5]benzodiazepin-10-one (mp 217° to 218° C.),
4-chloroacetyl-3-isopropyl-1-methyl-1,4,9,10-tetrahydropyrazolo[4,3-b][1,5]benzodiazepin-10-one,
4-chloroacetyl-1-methyl-1,4,9,10-tetrahydropyrazolo[4,3-b][1,5]benzodiazepin-10-one (mp 245° to 246° C. with decomposition),
4-chloroacetyl-1-ethyl-1,4,9,10-tetrahydropyrazolo[4,3-b][1,5]benzodiazepin-10-one and
4-chloroacetyl-1-isopropyl-1,4,9,10-tetrahydropyrazolo[4,3-b][1,5]benzodiazepin-10-one,
are obtained analogously by reacting chloroacetyl chloride with a corresponding amount of each of
1,3-dimethyl-1,4,9,10-tetrahydropyrazolo[4,3-b][1,5]benzodiazepin-10-one,
3-ethyl-1-methyl-1,4,9,10-tetrahydropyrazolo[4,3-b][1,5]benzodiazepin-10-one,
3-isopropyl-1-methyl-1,4,9,10-tetrahydropyrazolo[4,3-b][1,5]benzodiazepin-10-one,
1-methyl-1,4,9,10-tetrahydropyrazolo[4,3-b][1,5]benzodiazepin-10-one,
1-ethyl-1,4,9,10-tetrahydropyrazolo[4,3-b][1,5]benzodiazepin-10-one and
1-isopropyl-1,4,9,10-tetrahydropyrazolo[4,3-b][1,5]benzodiazepin-10-one, respectively.

EXAMPLE 15

5.0 g of 1,3-dimethyl-1,4,9,10-tetrahydropyrazolo[4,3-b][1,5]benzodiazepin-10-one, 5.2 g of 3-chloropropionyl chloride, 11 g of ground potassium carbonate and 60 ml of absolute dioxane are stirred at from 50° to 60° C. for 1.5 hours, and the solvent is then removed by distillation in vacuo. Ice water and hydrochloric acid are added to the residue to give pH 6, the mixture is allowed to stand overnight in a refrigerator and the resulting precipitate is recrystallized from ethyl acetate/cyclohexane. This yields 5.3 g of 4-(3-chloropropionyl)-1,3-dimethyl-1,4,9,10-tetrahydropyrazolo[4,3-b][1,5]benzodiazepin-10-one, mp 205° to 206.5° C. (dec.).

4-(3-Chloropropionyl)-1-ethyl-3-methyl-1,4,9,10-tetrahydropyrazolo[4,3-b][1,5]benzodiazepin-10-one,
4-(3-chloropropionyl)-1-isopropyl-3-methyl-1,4,9,10-tetrahydropyrazolo[4,3-b][1,5]benzodiazepin-10-one,
4-(3-chloropropionyl)-3-ethyl-1-methyl-1,4,9,10-tetrahydropyrazolo[4,3-b][1,5]benzodiazepin-10-one,
4-(3-chloropropionyl)-3-isopropyl-1-methyl-1,4,9,10-tetrahydropyrazolo[4,3-b][1,5]benzodiazepin-10-one,
4-(3-chloropropionyl)-1-methyl-1,4,9,10-tetrahydropyrazolo[4,3-b][1,5]benzodiazepin-10-one,
4-(3-chloropropionyl)-1-ethyl-1,4,9,10-tetrahydropyrazolo[4,3-b][1,5]benzodiazepin-10-one and
4-(3-chloropropionyl)-1-isopropyl-1,4,9,10-tetrahydropyrazolo[4,3-b][1,5]benzodiazepin-10-one
are obtained analogously by reacting 3-chloropropionyl chloride with a corresponding amount of each of
1-ethyl-3-methyl-1,4,9,10-tetrahydropyrazolo[4,3-b][1,5]benzodiazepin-10-one,
1-isopropyl-3-methyl-1,4,9,10-tetrahydropyrazolo[4,3-b][1,5]benzodiazepin-10-one,
3-ethyl-1-methyl-1,4,9,10-tetrahydropyrazolo[4,3-b][1,5]benzodiazepin-10-one,
3-isopropyl-1-methyl-1,4,9,10-tetrahydropyrazolo[4,3-b][1,5]benzodiazepin-10-one,
1-methyl-1,4,9,10-tetrahydropyrazolo[4,3-b][1,5]benzodiazepin-10-one,
1-ethyl-1,4,9,10-tetrahydropyrazolo[4,3-b][1,5]benzodiazepin-10-one and
1-isopropyl-1,4,9,10-tetrahydropyrazolo[4,3-b][1,5]benzodiazepin-10-one, respectively.

EXAMPLE 16

4-(2-chloropropionyl)-1,3-dimethyl-1,4,9,10-tetrahydropyrazolo-[4,3-b][1,5]benzodiazepin-10-one,
4-(2-chloropropionyl)-1-ethyl-3-methyl-1,4,9,10-tetrahydropyrazolo[4,3-b][1,5]benzodiazepin-10-one,
4-(2-chloropropionyl)-1-isopropyl-3-methyl-1,4,9,10-tetrahydropyrazolo[4,3-b][1,5]benzodiazepin-10-one,
4-(2-chloropropionyl)-3-ethyl-1-methyl-1,4,9,10-tetrahydropyrazolo[4,3-b][1,5]benzodiazepin-10-one,
4-(2-chloropropionyl)-3-isopropyl-1-methyl-1,4,9,10-tetrahydropyrazolo[4,3-b][1,5]benzodiazepin-10-one,
4-(2-chloropropionyl)-1-methyl-1,4,9,10-tetrahydropyrazolo[4,3-b][1,5]benzodiazepin-10-one, 4-(2-chloropropionyl)-1-ethyl-1,4,9,10-tetrahydropyrazolo[4,3-b][1,5]benzodiazepin-10-one and
4-(2-chloropropionyl)-1-isopropyl-1,4,9,10-tetrahydropyrazolo[4,3-b][1,5]benzodiazepin-10-one
are obtained analogously to Example 14 by reacting 2-chloropropionyl chloride with a corresponding amount of
1,3-dimethyl-1,4,9,10-tetrahydropyrazolo[4,3-b][1,5]benzodiazepin-10-one,
1-ethyl-3-methyl-1,4,9,10-tetrahydropyrazolo[4,3-b][1,5]benzodiazepin-10-one,
1-isopropyl-3-methyl-1,4,9,10-tetrahydropyrazolo[4,3-b][1,5]benzodiazepin-10-one,
3-ethyl-1-methyl-1,4,9,10-tetrahydropyrazolo[4,3-b][1,5]benzodiazepin-10-one,
3-isopropyl-1-methyl-1,4,9,10-tetrahydropyrazolo[4,3-b][1,5]benzodiazepin-10-one,
1-methyl-1,4,9,10-tetrahydropyrazolo[4,3-b][1,5]benzodiazepin-10-one,
1-ethyl-1,4,9,10-tetrahydropyrazolo[4,3-b][1,5]benzodiazepin-10-one and
1-isopropyl-1,4,9,10-tetrahydropyrazolo[4,3-b][1,5]benzodiazepin-10-one, respectively, and
4-(4-chlorobutyryl)-1,3-dimethyl-1,4,9,10-tetrahydropyrazolo[4,3-b][1,5]benzodiazepin-10-one and
4-(5-chlorovaleryl)-1,3-dimethyl-1,4,9,10-tetrahydropyrazolo[4,3-b][1,5]benzodiazepin-10-one
are obtained analogously to Example 14 by reacting 4-chlorobutyryl chloride and 5-chlorovaleryl chloride, respectively, with a corresponding amount of
1,3-dimethyl-1,4,9,10-tetrahydropyrazolo[4,3-b][1,5]benzodiazepin-10-one.

EXAMPLE 17

7.1 g of 4-[(2-aminophenyl)amino]-N,N,1,3-tetramethylpyrazole-5-carboxamide, 4.7 g of benzoic acid and 8 ml of dry xylene are heated at the boil for 75 minutes, and the solvent is then removed by distillation in vacuo. The resulting residue is dissolved in 70 ml of chloroform, and the thus-prepared organic solution is washed with sodium hydroxide and water, dried with magnesium sulfate and filtered through a layer of silica gel. This yields, as yellow crystals, 5.45 g of 1,3-dimethyl-1,4,9,10-tetrahydropyrazolo[4,3-b][1,5]benzodiazepin-10-one, mp 189° to 190° C.

Cyclization takes place in an analogous manner when other medium-strength acids, such as o-chlorobenzoic acid, nicotinic acid, m-toluic acid or chloroacetic acid, are employed instead of benzoic acid.

EXAMPLE 18

A melt obtained from 14.3 g of 4-[(2-aminophenyl)amino]-1-ethyl-N,N,3-trimethylpyrazole-5-carboxamide and 9.1 g of benzoic acid is stirred at 150° C. for 2.5 hours; 50 ml of chloroform are added to the hot melt, and the obtained solution is stirred thoroughly with sodium bicarbonate solution and water before being concentrated in vacuo. The resulting residue is chromatographed through a silica gel column using 3:7 petroleum ether (bp 50°/70° C.)/ethyl acetate. This yields, as yellow crystals, 8.2 g of 1-ethyl-3-methyl-1,4,9,10-tetrahydropyrazolo[4,3-b][1,5]benzodiazepin-10-one, mp 161° to 162° C.

1,3-Dimethyl-1,4,9,10-tetrahydropyrazolo[4,3-b][1,5]benzodiazepin-10-one,
is obtained analogously by heating
4-[(2-aminophenyl)amino]-N,N-diethyl-1,3-dimethylpyrazole-5-carboxamide,
4-[(2-aminophenyl)amino]-N,1,3-trimethyl-N-phenylpyrazole-5-carboxamide,
1-{(4-[(2-aminophenyl)amino]-1,3-dimethylpyrazol-5-yl)carbonyl}piperidine or
4-[(2-aminophenyl)amino]-N,1,3-trimethylpyrazole-5-carboxamide in the presence of benzoic acid.

EXAMPLE 19

8.3 g of 4-[(2-aminophenyl)amino]-1,3-dimethylpyrazole-5-carboxamide and 8.4 g of benzoic acid are heated at 125° C. for 45 minutes. The melt is cooled and stirred with dilute sodium bicarbonate solution; the yellow precipitate is filtered off and washed with water. This yields 7.1 g of 1,3-dimethyl-1,4,9,10-tetrahydropyrazolo[4,3-b][1,5]benzodiazepin-10-one, mp 189° to 190° C. (from ethyl acetate).

EXAMPLE 20

2.0 g of 4-[(2-aminophenyl)amino]-1,3-dimethylpyrazole-5-carboxylic acid methyl ester and 2.0 g of benzoic acid are heated at 120° C. for 1 hour and then at 140° C. for 2 hours, after which a thin layer chromatogram indicates complete reaction. The melt is cooled and stirred with warm sodium bicarbonate solution, and the precipitate (1.55 g) is filtered off and recrystallized from ethyl acetate and cyclohexane. This yields 1,3-dimethyl-1,4,9,10-tetrahydropyrazolo[4,3-b][1,5]benzodiazepin-10-one, mp 189° to 190° C.

1,3-Dimethyl-1,4,9,10-tetrahydropyrazolo[4,3-b][1,5]benzodiazepin-10-one is obtained analogously by heating
4-[(2-aminophenyl)amino]-1,3-dimethylpyrazole-5-carboxylic acid ethyl ester or
4-[(2-aminophenyl)amino]-1,3-dimethylpyrazole-5-carboxylic acid n-amyl ester
in the presence of benzoic acid.

EXAMPLE 21

1-Isopropyl-3-methyl-1,4,9,10-tetrahydropyrazolo[4,3-b][1,5]benzodiazepin-10-one,
3-ethyl-1-methyl-1,4,9,10-tetrahydropyrazolo[4,3-b][1,5]benzodiazepin-10-one (mp 164° to 165° C.),
3-isopropyl-1-methyl-1,4,9,10-tetrahydropyrazolo[4,3-b][1,5]benzodiazepin-10-one,
1-methyl-1,4,9,10-tetrahydropyrazolo[4,3-b][1,5]benzodiazepin-10-one (mp 201° to 203° C.),
1-ethyl-1,4,9,10-tetrahydropyrazolo[4,3-b][1,5]benzodiazepin-10-one and
1-isopropyl-1,4,9,10-tetrahydropyrazolo[4,3-b][1,5]benzodiazepin-10-one
are obtained analogously to Example 17 when
4-[(2-aminophenyl)amino]-1-isopropyl-N,N,3-trimethylpyrazole-5-carboxamide,
4-[(2-aminophenyl)amino]-3-ethyl-N,N,1-trimethylpyrazole-5-carboxamide,
4-[(2-aminophenyl)amino]-3-isopropyl-N,N,1-trimethylpyrazole-5-carboxamide,
4-[(2-aminophenyl)amino]-N,N,1-trimethylpyrazole-5-carboxamide,
4-[(2-aminophenyl)amino]-1-ethyl-N,N-dimethylpyrazole-5-carboxamide and
4-[(2-aminophenyl)amino]-1-isopropyl-N,N-dimethylpyrazole-5-carboxamide,
respectively, are heated in xylene in the presence of benzoic acid.

EXAMPLE 22

2.4 g of 1,3-dimethyl-4-[(2-nitrophenyl)amino]-pyrazole-5-carboxylic acid phenyl ester are hydrogenated in 150 ml of toluene and 5 ml of glacial acetic acid using 0.75 g of 10% strength palladium-on-charcoal at room temperature for 2.1 hours in a circulatory hydrogenation apparatus. The solution is filtered and concentrated in vacuo; the residue is chromatographed over a silica gel column using 1:1 petroleum ether (50°/70° C.)/ethyl acetate to yield 1.1 g of 1,3-dimethyl-1,4,9,10-tetrahydropyrazolo[4,3-b][1,5]benzodiazepin-10-one, mp 189° to 190° C.

When the phenyl ester is hydrogenated without adding glacial acetic acid, there is a slow uptake of hydrogen, and 4-[(2-aminophenyl)amino]-1,3-dimethyl-pyrazole-5-carboxylic acid phenyl ester is formed; this undergoes cyclization to yield the pyrazolobenzodiazepinone on addition of glacial acetic acid.

EXAMPLE 23

80 ml of dry dioxan and 8.3 g of triethylamine are added to 4-[(2-aminophenyl)amino]-1,3-dimethyl-pyrazole-5-carboxylic acid (the residue from Experiment 4); 8.8 of chloroformic acid ethyl ester are added dropwise at 0° C. over a period of 15 minutes, and the resulting mixture is stirred for a further 1.5 hours while warming up to room temperature. Sodium bicarbonate solution is added to the solution; the mixture is concentrated to dryness, and the residue is extracted by boiling it with chloroform. The solution is concentrated, and the residue is chromatographed over a silica gel column using 1:1 petroleum ether (50°/70° C.)/ethyl acetate to yield 7.5 g of 1,3-dimethyl-1,4,9,10-tetrahydropyrazolo[4,3-b][1,5-benzodiazepin-10-one, mp 180° to 190° C. (from toluene).

The following "Experiments" illustrate in greater detail the preparation of starting compounds (intermediate products).

A: 4-[(2-Aminophenyl)amino]-5-pyrazolecarboxylic acid derivatives

Experiment 1

4-[2-(Aminophenyl)amino]-N,N,1,3-tetramethyl-pyrazole-5-carboxamide 85.4 g of N,N,1,3-tetramethyl-4-[(2-nitrophenyl)amino]pyrazole-5-carboxamide in 1,100 ml of methanol are hydrogenated over 8.5 g of 10% strength palladium-on-charcoal at atmospheric pressure in a circulatory hydrogenation apparatus for 3.5 hours at 25° C. The mixture is filtered; the solution is concentrated to dryness, and the residue is stirred with a mixture consisting of 80 ml of petroleum ether (bp 50° to 70° C.) and 40 ml of ethyl acetate. This yields 75 g of 4-[2-(aminophenyl)amino]-N,N,1,3-tetramethylpyrazole-5-carboxamide (initial mp 137° to 139° C.), which, on standing, undergoes conversion into a product of mp 171° to 172° C.
4-[(2-Aminophenyl)amino]-N,1,3-trimethylpyrazole-5-carboxamide (mp 151.5° to 152.5° C.),
4-[(2-aminophenyl)amino]-N,N-diethyl-1,3-dimethyl-pyrazole-5-carboxamide,
1-[{4-[(2-aminophenyl)amino]-1,3-dimethylpyrazol-5-yl}carbonyl]piperidine,
4-[(2-aminophenyl)amino]-1-ethyl-N,N,3-trimethyl-pyrazole-5-carboxamide (mp 144° to 145° C.),
4-[(2-aminophenyl)amino]-1-isopropyl-N,N,3-trimethylpyrazole-5-carboxamide,
4-[(2-aminophenyl)amino]-N,N,1-trimethylpyrazole-5-carboxamide (mp 142° to 144° C.),
4-[(2-aminophenyl)amino]-1-ethyl-N,N-dimethyl-pyrazole-5-carboxamide,
4-[(2-aminophenyl)amino]-1-isopropyl-N,N-dimethyl-pyrazole-5-carboxamide,
4-[(2-aminophenyl)amino]-3-ethyl-N,N,1-trimethyl-pyrazole-5-carboxamide,
4-[(2-aminophenyl)amino]-3-isopropyl-N,N,1-trimethylpyrazole-5-carboxamide and
4-[(2-aminophenyl)amino]-N,1,3-trimethyl-N-phenyl-pyrazole-5-carboxamide are obtained analogously from
N,1,3-trimethyl-4-[(2-nitrophenyl)amino]pyrazole-5-carboxamide,
N,N-diethyl-1,3-dimethyl-4-[(2-nitrophenyl)amino]-pyrazole-5-carboxamide,
1-[{1,3-dimethyl-4-[(2-nitrophenyl)amino]pyrazol-5-yl}carbonyl]piperidine,
1-ethyl-N,N,3-trimethyl-4-[(2-nitrophenyl)amino]-pyrazole-5-carboxamide,
1-isopropyl-N,N,3-trimethyl-4-[(2-nitrophenyl)amino]-pyrazole-5-carboxamide,
N,N,1-trimethyl-4-[(2-nitrophenyl)amino]pyrazole-5-carboxamide,
1-ethyl-N,N-dimethyl-4-[(2-nitrophenyl)amino]-pyrazole-5-carboxamide,
1-isopropyl-N,N-dimethyl-4-[(2-nitrophenyl)amino]-pyrazole-5-carboxamide,
3-ethyl-N,N,1-trimethyl-4-[(2-nitrophenyl)amino]-pyrazole-5-carboxamide,
3-isopropyl-N,N,1-trimethyl-4-[(2-nitrophenyl)amino]-pyrazole-5-carboxamide and
N,1,3-trimethyl-4-[(2-nitrophenyl)amino]-N-phenyl-pyrazole-5-carboxamide, respectively, by reducing the nitro group.

Experiment 2

4-[(2-Aminophenyl)amino]-1,3-dimethylpyrazole-5-carboxamide 8.6 g of 1,3-dimethyl-4-[(2-nitrophenyl)amino]-pyrazole-5-carboxamide in 400 ml of ethanol are hydrogenated over 0.8 g of 10% strength palladium-on-charcoal for 1 hour at 50° C. analogously to Experiment 1. The mixture is filtered; the filtrate is concentrated to dryness, and the residue from evaporation is recrystallized from 160 ml of ethyl acetate and 120 ml of cyclohexane to yield 7.1 g of 4-[(2-aminophenyl)amino]-1,3-dimethylpyrazole-5-carboxamide, mp 182° to 184° C. (dec.).

Experiment 3

4-[(2-Aminophenyl)amino]-1,3-dimethylpyrazole-5-carboxylic acid n-amyl ester 15 g of 1,3-dimethyl-4-[(2-nitrophenyl)amino]-pyrazole-5-carboxylic acid n-amyl ester in 250 ml of ethanol are hydrogenated at room temperature for 5 hours in a circulatory hydrogenation apparatus at atmospheric pressure, using 4 g of 10% strength palladium-on-charcoal, after which a thin layer chromatogram indicates quantitative conversion. The catalyst is filtered off, and the solution is concentrated in vacuo to yield, as an oily residue, 13.5 g of 4-[(2-aminophenyl)amino]-1,3-dimethylpyrazole-5-carboxylic acid n-amyl ester.
4-[(2-Aminophenyl)amino]-1,3-dimethylpyrazole-5-carboxylic acid methyl ester (mp 100° to 101.5° C.), 4-[(2-aminophenyl)amino]-1,3-dimethylpyrazole-5-carboxylic acid ethyl ester and
4-[(2-aminophenyl)amino]-1,3-dimethylpyrazole-5-carboxylic acid phenyl ester
are obtained analogously from
1,3-dimethyl-4-[(2-nitrophenyl)amino]pyrazole-5-carboxylic acid methyl ester,
1,3-dimethyl-4-[(2-nitrophenyl)amino]pyrazole-5-carboxylic acid ethyl ester and
1,3-dimethyl-4-[(2-nitrophenyl)amino]pyrazole-5-carboxylic acid phenyl ester, respectively,
by reducing the nitro group (hydrogenation) in methanol.

Experiment 4

4-[(2-Aminophenyl)amino]-1,3-dimethylpyrazole-5-carboxylic acid

A solution of 2.9 g of sodium hydroxide in 100 ml of degassed ethanol is added at room temperature (20° C.) to 13 g of 1,3-dimethyl-4-[(2-aminophenyl)amino]-pyrazole-5-carboxylic acid n-amyl ester, and the mixture is stirred for 3 hours at room temperature. The pH of the solution is adjusted to 9 by means of dilute hydrochloric acid; the alcohol is removed by distillation; the aqueous solution is extracted by shaking it with methylene chloride; and the aqueous solution is adjusted to pH 7 and concentrated in vacuo at 60° C. 4-(2-Aminophenylamino)-1,3-dimethylpyrazole-5-carboxylic acid, which is partially oily, is thus obtained as the residue, mixed with inorganic salts.

B: 4-[(2-Nitrophenyl)amino]pyrazole-5-carboxylic acid derivatives

Experiment 5

N,N,1,3-Tetramethyl-4-[(2-nitrophenyl)amino]-pyrazole-5-carboxamide 10.5 g of sodium hydride (75% strength in paraffin oil) is added under nitrogen to a solution of 26.5 g of 4-amino-N,N,1,3-tetramethylpyrazole-5-carboxamide in 100 ml of dimethylformamide; a solution of 28 g of 1-fluoro-2-nitrobenzene in 25 ml of dimethylformamide is added dropwise at 40° to 45° C. to the obtained suspension over a period of 2 hours. The thus prepared mixture is stirred for a further 4 hours at 40° C.; the obtained red solution is neutralized by adding glacial acetic acid, and the solvent is removed by distillation in vacuo. The formed residue is subjected to steam distillation, and the residue is then dissolved in 9:1 methylene chloride/methanol; the produced solution is chromatographed over silica gel to yield 35.0 g of yellow crystals of N,N,1,3-tetramethyl-4-[(2-nitrophenyl)amino]-pyrazol-5-carboxamide, mp 144° to 146° C. (from ethyl acetate).
N,N-Diethyl-1,3-dimethyl-4-[(2-nitrophenyl)amino]-pyrazole-5-carboxamide,
1-[{1,3-dimethyl-4-[(2-nitrophenyl)amino]pyrazol-5-yl}carbonyl]piperidine,
1-ethyl-N,N,3-trimethyl-4-[(2-nitrophenyl)amino]-pyrazole-5-carboxamide (mp 97° to 98° C.),
1-isopropyl-N,N,3-trimethyl-4-[(2-nitrophenyl)amino]-pyrazole-5-carboxamide,
N,N,1-trimethyl-4-[(2-nitrophenyl)amino]pyrazole-5-carboxamide (mp 138.5° to 140° C.),
1-ethyl-N,N-dimethyl-4-[(2-nitrophenyl)amino]-pyrazole-5-carboxamide,
1-isopropyl-N,N-dimethyl-4-[(2-nitrophenyl)amino]-pyrazole-5-carboxamide,
3-ethyl-N,N,1-trimethyl-4-[(2-nitrophenyl)amino]-pyrazole-5-carboxamide (mp 114° to 115° C.) and
3-isopropyl-N,N,1-trimethyl-4-[(2-nitrophenyl)amino]-pyrazole-5-carboxamide
are obtained analogously from
4-amino-N,N-diethyl-1,3-dimethylpyrazole-5-carboxamide,
1-[(4-amino-1,3-dimethylpyrazol-5-yl)carbonyl]piperidine,
4-amino-1-ethyl-N,N,3-trimethylpyrazole-5-carboxamide,
4-amino-1-isopropyl-N,N,3-trimethylpyrazole-5-carboxamide,
4-amino-N,N,1-trimethylpyrazole-5-carboxamide,
4-amino-1-ethyl-N,N-dimethylpyrazole-5-carboxamide,
4-amino-1-isopropyl-N,N-dimethylpyrazole-5-carboxamide,
4-amino-3-ethyl-N,N,1-trimethylpyrazole-5-carboxamide and
4-amino-3-isopropyl-N,N,1-trimethylpyrazole-5-carboxamide, respectively,
by reaction with a corresponding amount of 1-fluoro-2-nitrobenzene.

Experiment 6

N,N,1,3-Tetramethyl-4-[(2-nitrophenyl)amino]-pyrazole-5-carboxamide 1.1 g of sodium hydride (75% strength in paraffin oil) and then 3.5 g of 1-chloro-2-nitrobenzene are added under nitrogen to a solution of 2.0 g of 4-amino-N,N,1,3-tetramethylpyrazole-5-carboxamide in 20 ml of dimethylformamide; the mixture is stirred for 4 hours at 40° C. and for 24 hours at room temperature before being worked up analogously to Experiment 5. This yields 2.0 g of N,N,1,3-tetramethyl-4-[(2-nitrophenyl)amino]pyrazole-5-carboxamide, mp 144° to 146° C.

Experiment 7

N,N,1,3-Tetramethyl-4-[(2-nitrophenyl)amino]-pyrazole-5-carboxamide 2.0 g of 4-amino-N,N,1,3-tetramethylpyrazole-5-carboxamide, 2.0 g of 1-fluoro-2-nitrobenzene and 1.8 g of N-ethylmorpholine are heated at 150° C. for 12 hours. Dilute hydrochloric acid is added to the reaction product, and the crystalline residue is filtered off, dried and thoroughly stirred with a little petroleum ether (bp 40° C.). This yields 2.5 g of N,N,1,3-tetramethyl-4-[(2-nitrophenyl)amino]pyrazole-5-carboxamide, mp 144° to 146° C. (from ethyl acetate). N,1,3-Trimethyl-4-[(2-nitrophenyl)amino]pyrazole-5-carboxamide is obtained analogously from 4-amino-N,1,3-trimethylpyrazole-5-carboxamide hydrochloride, N-ethylmorpholine and 1-fluoro-2-nitrobenzene, as yellow crystals, mp 223° to 225° C.

Experiment 8

1,3-Dimethyl-4-[(2-nitrophenyl)amino]pyrazole-5-carboxamide

A mixture consisting of 10.35 g of 4-amino-1,3-dimethylpyrazole-5-carboxamide hydrochloride, 22.4 g of 1-bromo-2-nitrobenzene, 15 g of ground potassium carbonate, 2.7 g of copper(I) chloride and 55 ml of dimethylformamide is homogenized by treatment with ultrasonic sound and is warmed at 90° C. for 1 hour. The solvent is removed by distillation in vacuo; the residue is chromatographed over silica gel (using a 93:7 mixture of methylene chloride and methanol) and is recrystallized from toluene. This yields 10.0 g of yellow crystals of 1,3-dimethyl-4-[(2-nitrophenyl)amino]pyrazole-5-carboxamide, mp 232° to 233° C.

N,1,3-Trimethyl-4-[(2-nitrophenyl)amino]pyrazole-5-carboxamide (mp 223° to 225° C.) is obtained analogously from 4-amino-N,1,3-trimethylpyrazole-5-carboxamide hydrochloride by reacting the latter with 1-bromo-2-nitrobenzene.

Experiment 9

1,3-Dimethyl-4-[(2-nitrophenyl)amino]pyrazole-5-carboxylic acid n-amyl ester 16 g of 4-amino-1,3-dimethylpyrazole-5-carboxylic acid ethyl ester, 36 g of 1-bromo-2-nitrobenzene, 24 g of anhydrous potassium carbonate and 150 ml of n-amyl alcohol are heated for 12 hours with slow removal of the water of reaction by distillation through a short column, 8.2 g of copper powder and 8.2 g of copper(I) chloride, each divided into 4 portions, being added. The reaction mixture is cooled and diluted with 250 ml of ethyl acetate; the inorganic salts are filtered off; the filtrate is concentrated, and the resulting residue is chromatographed over a silica gel column using 4:1 petroleum ether (50°/70° C.)/ethyl acetate. As a result of transesterification with the solvent during reaction, the main fraction isolated is not the corresponding ethyl ester, but 20 g of oily 1,3-dimethyl-4-[(2-nitrophenyl)amino]pyrazole-5-carboxylic acid n-amyl ester, mp 60° to 62° C. (from methanol/water).

Experiment 10

1,3-Dimethyl-4-[(2-nitrophenyl)amino]pyrazole-5-carboxylic acid 4.05 g of 1,3-dimethyl-4-[(2-nitrophenyl)amino]pyrazole-5-carboxylic acid n-amyl ester (Experiment 9) and a solution of 0.7 g of sodium hydroxide in 80 ml of ethanol are stirred for 4 hours at 40° C. in a nitrogen atmosphere. The solution is buffered to pH 9–10 with glacial acetic acid; the mixture is concentrated in vacuo, and water is added to the residue. This mixture is extracted by shaking it with methylene chloride, and the aqueous solution is acidified with dilute hydrochloric acid. This yields 2.7 g of 1,3-dimethyl-4-[(2-nitrophenyl)amino]pyrazole-5-carboxylic acid, mp 253° to 254° C. (dec.).

Experiment 11

1,3-Dimethyl-4-[(2-nitrophenyl)amino]pyrazole-5-carboxylic acid chloride 2.6 g of 1,3-dimethyl-4-[(2-nitrophenyl)amino]pyrazole-5-carboxylic acid and 10 ml of thionyl chloride are stirred at 80° C. for 3 hours; the solution is concentrated; 10 ml of toluene are added, and the mixture is re-concentrated, this procedure being carried out 3 times. 2.9 g of 1,3-dimethyl-4-[(2-nitrophenyl)amino]pyrazole-5-carboxylic acid chloride are thus obtained as an orange-colored oil.

Experiment 12

1,3-Dimethyl-4-[(2-nitrophenyl)amino]pyrazole-5-carboxylic acid phenyl ester

The carboxylic acid chloride from Experiment 11 is warmed with 5 ml of absolute dioxane and 1.6 g of sodium phenolate for 30 minutes at 80° C. The obtained solution is filtered and concentrated. Toluene is added; the mixture is extracted several times by shaking it with water, and the solvent is removed by distillation in vacuo. 3.0 g of 1,3-dimethyl-4-[(2-nitrophenyl)amino]pyrazole-5-carboxylic acid phenyl ester are thus obtained as an oil.

Experiment 13

1,3-Dimethyl-[4-(2-nitrophenyl)amino]pyrazole-5-carboxylic acid methyl ester 13.0 g of 4-amino-1,3-dimethylpyrazole-5-carboxylic acid methyl ester, 32.0 g of 1-bromo-2-nitrobenzene, 10.7 g of anhydrous potassium carbonate, 8.0 g of copper(I) chloride (added in 3 portions) and 75 ml of dimethylformamide are heated at 150° C. for 9 hours. The solvent is removed by distillation in vacuo, and the residue is chromatographed over silica gel using 1:1 cyclohexane/ethyl acetate. This yields 3.1 g of 1,3-dimethyl-[4-(2-nitrophenyl)amino]pyrazole-5-carboxylic acid methyl ester, mp 127° to 129° C., and, as a by-product, 1,3-dimethyl-4-[(2-nitrophenyl)amino]pyrazole, mp 171° to 173° C.

Experiment 14

N,1,3-Trimethyl-4-[(2-nitrophenyl)amino]-N-phenylpyrazole-5-carboxamide 2.7 g of N-methylaniline are added dropwise to a solution of 2.95 g of 1,3-dimethyl-4-[(2-nitrophenyl)amino]pyrazole-5-carboxylic acid chloride in 10 ml of dioxane, and the resulting mixture is warmed at 90° C. for 1 hour. The solution is concentrated in vacuo, and water and a little dilute hydrochloric acid are added to yield 3.1 g of N,1,3-trimethyl-4-[(2-nitrophenyl)amino]-N-phenylpyrazole-5-carboxamide.

N,N-Diethyl-1,3-dimethyl-4-[(2-nitrophenyl)amino]-pyrazole-5-carboxamide,

1-[{1,3-dimethyl-4-[(2-nitrophenyl)amino]pyrazol-5-yl}carbonyl]piperidine and

N,1,3-trimethyl-4-[(2-nitrophenyl)amino]pyrazole-5-carboxamide are obtained analogously by reacting the acid chloride with diethylamine, piperidine or methylamine.

C: 4-Aminopyrazole-5-carboxylic acid derivatives

Experiment 15

4-Amino-N,N,1,3-tetramethylpyrazole-5-carboxamide 19.0 g of N,N,1,3-tetramethyl-4-nitropyrazole-5-carboxamide in 400 ml of methanol are hydrogenated in the presence of 2.0 g of 10% strength palladium-on-charcoal in an autoclave at a hydrogen pressure of from 80 to 110 bars (8,000 to 11,000 kPa) for 8 hours at room temperature. The mixture is filtered, and the solvent is removed by distillation in vacuo to yield 16.1 g of crystalline 4-amino-N,N,1,3-tetramethylpyrazole-5-carboxamide, mp 116° to 118° C. (from ethyl acetate).

4-Amino-N,1,3-trimethylpyrazole-5-carboxamide (hydrochloride mp 242° to 244° C.), 4-amino-1-ethyl-N,N,3-trimethylpyrazole-5-carboxamide (mp 81° to 82° C.), 4-amino-N,N-diethyl-1,3-dimethylpyrazole-5-carboxamide, 1-[(4-amino-1,3-dimethylpyrazol-5-yl)carbonyl]piperidine, 4-amino-N,N,1-trimethylpyrazole-5-carboxamide (mp 127° to 133° C.), 4-amino-1-ethyl-N,N-dimethylpyrazole-5-carboxamide,
4-amino-1-isopropyl-N,N-dimethylpyrazole-5-carboxamide,
4-amino-3-ethyl-N,N,1-trimethylpyrazole-5-carboxamide and
4-amino-3-isopropyl-N,N,1-trimethylpyrazole-5-carboxamide are obtained analogously by hydrogenating
N,1,3-trimethyl-4-nitropyrazole-5-carboxamide,
1-ethyl-N,N,3-trimethyl-4-nitropyrazole-5-carboxamide,
N,N-diethyl-1,3-dimethyl-4-nitropyrazole-5-carboxamide,
1-[(1,3-dimethyl-4-nitropyrazol-5-yl)carbonyl]piperidine,
N,N,1-trimethyl-4-nitropyrazole-5-carboxamide,
1-ethyl-N,N-dimethyl-4-nitropyrazole-5-carboxamide,
1-isopropyl-N,N-dimethyl-4-nitropyrazole-5-carboxamide,
3-ethyl-N,N,1-trimethyl-4-nitropyrazole-5-carboxamide and
3-isopropyl-N,N,1-trimethyl-4-nitropyrazole-5-carboxamide, respectively.

Experiment 16

4-Amino-1,3-dimethylpyrazole-5-carboxamide (a) 10.5 g of 1,3-dimethyl-4-nitropyrazole-5-carboxamide in 150 ml of methanol are hydrogenated over 1.0 g of 10% strength palladium-on-charcoal in an autoclave at a hydrogen pressure of 50 bars for 2 hours at 70° C. The mixture is filtered and the filtrate is concentrated to dryness in vacuo. The free base (mp 155° to 157° C. after recrystallization from ethyl acetate/cyclohexane) is dissolved in ethanol, and 7.4 g of the hydrochloride (mp 232° to 234° C. with decomposition) are precipitated by means of an ethereal solution of hydrogen chloride.

(b) 1.1 ml of hydrazine hydrate are added dropwise at 60° to 75° C. to a suspension of 2.0 g of 1,3-dimethyl-4-nitropyrazole-5-carboxamide and approximately 0.2 g of moist Raney nickel in 15 ml of ethanol; the solution is kept at the boil for 1.5 hours and is filtered. The filtrate is concentrated to dryness in vacuo, and 1.3 g of the hydrochloride, mp 232° to 234° C. (dec.), are precipitated by means of an ethereal solution of hydrogen chloride.

Experiment 17

4-Amino-1,3-dimethylpyrazole-5-carboxylic acid ethyl ester 20 g of 1,3-dimethyl-4-nitropyrazole-5-carboxylic acid ethyl ester in 250 ml of ethanol are hydrogenated over 4 g of 10% strength palladium-on-charcoal for 5.5 hours in a circulatory hydrogenation apparatus at atmospheric pressure and at room temperature. The solution is concentrated, and the residue is induced to crystallize by adding petroleum ether (50°/70° C.). This yields 15.6 g of 4-amino-1,3-dimethylpyrazole-5-carboxylic acid ethyl ester, mp 55.5° to 56.5° C.
4-Amino-1,3-dimethylpyrazole-5-carboxylic acid methyl ester (mp 76° to 78° C.; hydrochloride, mp 183° to 185° C. with decomposition) and
4-amino-1,3-dimethylpyrazole-5-carboxylic acid n-amyl ester (hydrochloride, mp 131° to 133° C.)
are obtained analogously from
1,3-dimethyl-4-nitropyrazole-5-carboxylic acid methyl ester and
1,3-dimethyl-4-nitropyrazole-5-carboxylic acid n-amyl ester, respectively.

D: 4-Nitropyrazole-5-carboxylic acid derivatives

Experiment 18

N,N,1,3-Tetramethyl-4-nitropyrazole-5-carboxamide

A solution of 40 g of 1,3-dimethyl-4-nitropyrazole-5-carboxylic acid chloride in 50 ml of methylene chloride is added dropwise at from 10° to 20° C., while cooling, to 43 g of a 40% strength aqueous solution of dimethylamine; stirring is continued for a further 20 minutes. The resulting mixture is rendered alkaline with potassium carbonate; the organic layer is separated off, and the aqueous phase is extracted by shaking it with methylene chloride. The organic solution is dried and concentrated, and the residue is triturated with petroleum ether (bp 40° to 70° C.) to yield 38.3 g of N,N,1,3-tetramethyl-4-nitropyrazole-5-carboxamide, mp 57° to 59.5° C., which is converted into a product of mp 114° to 115.5° C. on recrystallization from cyclohexane.
N,1,3-Trimethyl-4-nitropyrazole-5-carboxamide (mp 158° to 160° C.),
1-ethyl-N,N,3-trimethyl-4-nitropyrazole-5-carboxamide (mp 59° to 60.5° C.),
1-[(1,3-dimethyl-4-nitropyrazol-5-yl)carboxyl]piperidine,
N,N,1-trimethyl-4-nitropyrazole-5-carboxamide (mp 104° to 119° C.),
1-ethyl-N,N,-dimethyl-4-nitropyrazole-5-carboxamide,
1-isopropyl-N,N-dimethyl-4-nitropyrazole-5-carboxamide,
3-ethyl-N,N,1-trimethyl-4-nitropyrazole-5-carboxamide (mp 91° to 92° C.),
3-isopropyl-N,N,1-trimethyl-4-nitropyrazole-5-carboxamide and
4-[(1-ethyl-3-methyl-4-nitropyrazol-5-yl)]carbonylmorpholine
are obtained analogously from the corresponding 4-nitropyrazole-5-carboxylic acid chlorides and amines.

Experiment 19

1,3-Dimethyl-4-nitropyrazole-5-carboxamide 27.2 g of 1,3-dimethyl-4-nitropyrazole-5-carbonitrile and 65 ml of concentrated sulfuric acid are stirred at 80° C. for 6 hours. The mixture is poured into 700 g of ice and water, and the precipitate is filtered off and suspended in ice-water; the suspension is neutralized with sodium bicarbonate to yield 27.3 g of 1,3-dimethyl-4-nitropyrazole-5-carboxamide, mp 164° to 165° C.

Experiment 20

1,3-Dimethyl-4-nitropyrazole-5-carboxylic acid ethyl ester 44.6 g of phosphorus pentachloride are added in portions to 37 g of 1,3-dimethyl-4-nitropyrazole-5-carboxylic acid, and in the course of the addition the batch gradually becomes liquid. It is heated to a bath temperature of 100° C., while stirring; after stirring for 1 hour, it is concentrated in a rotary evaporator, and toluene is added to the mixture. The latter is reconcentrated, this procedure being carried out 3 times. 37 ml of absolute ethanol are added, while cooling, to the crystalline residue of 1,3-dimethyl-4-nitropyrazole-5-carboxylic acid chloride; the resulting solution is warmed at 50° C. for 1 hour and is concentrated in vacuo. 300 ml of ethyl acetate are added to the residue; the organic solution is extracted by shaking it with sodium bicarbonate solution and is concentrated. This yields 41.2 g of 1,3-dimethyl-4-nitropyrazole-5-carboxylic acid ethyl ester, mp 47° to 48° C.

1,3-Dimethyl-4-nitropyrazole-5-carboxylic acid methyl ester (mp 71° to 72° C.) and 1,3-dimethyl-4-nitropyrazole-5-carboxylic acid n-amyl ester (an oil)

are obtained analogously from 1,3-dimethyl-4-nitropyrazole-5-carboxylic acid chloride and the corresponding alcohol.

Experiment 21

1-Methyl-4-nitropyrazole-5-carboxylic acid 18.8 g of 1-methylpyrazole-5-carboxylic acid (mp 227° to 228° C.) are stirred in a mixture consisting of 23.5 of 100% strength nitric acid and 17 ml of 25% strength oleum for 8 hours at from 55° to 60° C. and for 4.5 hours at from 70° to 75° C. The mixture is poured onto ice and extracted with 9:1 methylene chloride/ethanol. The extract is concentrated. This yields 27 g of 1-methyl-4-nitropyrazole-5-carboxylic acid, mp 162° to 164° C., with decomposition (from ethyl acetate).

Experiment 22

3-Isopropyl-1-methyl-4-nitropyrazole-5-carboxylic acid (a) A mixture of 148 g of oxalic acid diethyl ester and 86 g of acetone is added dropwise, at from 6° to 20° C. (while cooling slightly) to a solution of 23.0 g of sodium in absolute ethanol, and the crystallizing mixture is allowed to stand overnight. It is diluted with 500 ml of ethanol and filtered to yield 185 g of sodium 5-methyl-2,4-dioxohexanoate.

(b) 44.6 g of glacial acetic acid in 200 ml of ethanol and then, at $-3°$ to 0° C., 52.9 g of hydrazine hydrate are added dropwise to 180 g of the sodium salt from (a) in 800 ml of ethanol; the solvent is removed by distillation in vacuo; water is added, and the mixture is extracted with chloroform. The solvent is removed by distillation in vacuo; toluene is added; the mixture is concentrated, and the crystalline residue is dried over paraffin and rapidly stirred in 600 ml of ice-water. This yields 141 g of 5-isopropyl-1-methylpyrazole-3-carboxylic acid ethyl ester, mp 70.5° to 71° C. (from water).

(c) 5.9 g of the ester from (b) and 4.1 g of diemthyl sulfate are warmed at 90° C. for 2.5 hours; 18 ml of 6 N sodium hydroxide solution are then added dropwise, and the mixture is stirred at 80° C. for 2.5 hours and acidified, while warm, with concentrated hydrochloric acid; the precipitate is filtered off and stirred in ice-water to yield 4.1 g of 3-isopropyl-1-methylpyrazole-5-carboxylic acid, mp 159° to 160° C. (from dioxane/cyclohexane).

(d) 4 g of the carboxylic acid from (c), 3.6 ml of 100% strength nitric acid and 4.2 ml of 25% strength oleum are stirred for 20 hours at 60° C. and for 48 hours at room temperature. The mixture is poured onto ice to yield 3-isopropyl-1-methyl-4-nitropyrazole-5-carboxylic acid.

The examples which follow describe the formulation of a compound according to the invention to prepare medicaments.

EXAMPLE 24

10,000 tablets, each containing 20 mg of active compound, are prepared from the following ingredients:

200 g of 1,3-dimethyl-4-[(4-methylpiperazin-1-yl)-acetyl]-1,4,9,10-tetrahydropyrazolo[4,3-b][1,5]benzodiazepin-10-one, 900 g of maize starch, 500 g of lactose, 30 g of amorphous silica and 40 g of sodium lauryl sulfate are mixed and put through a sieve. This mixture is moistened with a solution of 50 g of polyvinylpyrrolidone (average molecular weight 25,000) in 320 ml of alcohol and is granulated through a sieve of 1.25 mm mesh width. The granules are dried at 40° and mixed with 160 g of pectin, 100 g of talc and 20 g of magnesium stearate. This mixture is compressed into tablets weighing 200 mg and having a diameter of 8 mm.

EXAMPLE 25

100,000 capsules, each containing 30 mg of active compound, are prepared from the following ingredients:

3,000 g of 1,3-dimethyl-4-[(4-methylpiperazin-1-yl)acetyl]-1,4,9,10-tetrahydropyrazolo[4,3-b][1,4]benzodiazepin-10-one are mixed with 5,000 g of neutral oil (Miglyol ® to 812), and the mixture is filled into soft gelatin capsules.

EXAMPLE 26

100,000 capsules, each containing 30 mg of active compound, are prepared from the following ingredients:

1,500 g of 1,3-dimethyl-4-[(4-methylpiperazin-1-yl)acetyl]-1,4,9,10-tetrahydropyrazolo[4,3-b][1,5]benzodiazepin-10-one and 1,500 g of magnesium trisilicate are mixed with 5,000 g of neutral oil (Miglyol ® to 812), and the mixture is filled into soft gelatin capsules.

Pharmacology

The excellent protective action on the stomach of the pharmacologically-active pyrazolobenzodiazepinones is demonstrated by a test using so-called Shay rats as a model. The test establishes that the compounds according to the invention are clearly superior to the known commercial product, carbenoxolone (1), with regard to protective action on the stomach and toxicity, as can be shown, for example, by a comparison of (1) and 1,3-dimethyl-4-[(4-methylpiperazin--yl)acetyl]-1,4,9,10-tetrahydropyrazolo[4,3-b][1,5]-benzodiazepin-10-one (2).

TABLE I

| | The anti-ulcerogenic action and toxicity of pyrazolobenzodiazepinones | | | |
|---|---|---|---|---|
| Serial No. | Toxicity $LD_{50}$ [mg/kg] administered intravenously to mice | Protective action on the stomach $ED_{50}$ [mg/kg] administered perorally to rats | TQ $LD_{50}/ED_{50}$ | % inhibition of stomach secretion* in rats |
| 1 | 290 | ~70 | 4.1 | 7 |
| 2 | 210 | 2.5 | 84.0 | 20 |

$ED_{50}$ = the dose which reduces the ulcer index for the group treated by 50% compared with the control group
$LD_{50}$ = the dose at which 50% of the animals die
TQ = the therapeutic quotient $LD_{50}/ED_{50}$
*% inhibition = *inhibition (in %) of stomach secretion 4 hours after administration of the anti-ulcerogenic $ED_{50}$*

It should be emphasized particularly that, although an $ED_{50}$ can still be determined for compound 1, the dose/action curve then flattens out very considerably so that, even at 300 mg/kg, it is not possible to achieve any substantial increase in the anti-ulcerogenic action.

In contrast to this, the action of compound 2 depends strictly on the dose; inhibitory effects of up to 95% (30 mg/kg) are achieved.

The anti-ulcerogenic action is tested by a method using the so-called Shay rats:

Ulcers are provoked in rats which have been starved for 24 hours (female rats, 180 to 200 g, 4 animals in a cage with a high grille) by means of a pylorus ligature (under anaesthesia with diethyl ether) and oral administration of 100 mg/10 ml/kg of acetylsalicylic acid. The substances to be tested are administered orally (10 ml/kg) 1 hour before the pylorus ligature. The closure of the wound is effected by means of Michel's clips. The animals are killed 4 hours afterwards under ether anaesthesia by dislocating the atlas, and the stomach is cut out. The stomach is opened longitudinally and is fixed on a cork slab, the quantity of gastric juice secreted (volume) having been determined beforehand; the number and size (=diameter) of ulcers present are determined by means of a stereomicroscope at a 10-fold magnification. The product of the degree of severity (in accordance with the following rating scale) and the number of the ulcers is used as an individual ulcer index.

| Point rating: | | |
|---|---|---|
| no ulcers | | 0 |
| ulcer diameter | 0.1–1.4 mm | 1 |
| | 1.5–2.4 mm | 2 |
| | 2.5–3.4 mm | 3 |
| | 3.5–4.4 mm | 4 |
| | 4.5–5.4 mm | 5 |
| | >5.5 mm | 6 |

The reduction in the average ulcer index in each group treated compared with that of the control group (=100%) is used as a measure of the anti-ulcerogenic effect. The $ED_{50}$ indicates the dose which reduces the average ulcer index by 50%.

Determination of toxicity

The toxicity investigations are carried out on female NMRI mice (body weight 22 to 26 g). The animals (5 animals per dose) receive feed and water ad lib. Various doses of the substances are administered intravenously (duration of injection 1 minute). The observation period is 7 days. The $LD_{50}$ (the dose at which 50% of the animals die) is determined by means of a linear regression.

The invention and its advantages are readily understood from the proceding description. Various changes may be made in the synthesis, the intermediates, the pharmacologically-active final products, the dosage forms, the medicament compositions and the mode of administration without departing from the spirit and scope of the invention or sacrificing its material advantages. The hereinbefore described aspects of the subject invention are merely illustrative of preferred embodiments.

What is claimed is:

1. A pyrazolobenzodiazepinone of the formula

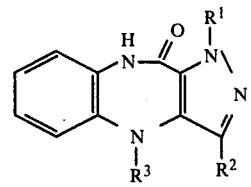

wherein
$R^1$ denotes alkyl with from 1 to 4 carbon atoms,
$R^2$ denotes —H or alkyl with from 1 to 4 carbon atoms,
$R^3$ denotes —H or —CO—A—$R^4$,
$R^4$ denotes halo or —N($R^5$) $R^6$,
$R^5$ denotes alkyl with from 1 to 4 carbon atoms, alkenyl with from 3 to 5 carbon atoms or, together with $R^6$ and the nitrogen atom to which both are bound, morpholino, pyrrolidino, piperidino, hexahydroazepin-1-yl, piperazin-1-yl which is optionally substituted in the 4-position by methyl, ethyl or benzyl, 2,4-dimethylpiperazin-1-yl or hexahydro-1H-1,4-diazepin-1-yl substituted in the 4-position by methyl or ethyl,
$R^6$ has one of the meanings of $R^5$, is —($CH_2$)$_m$—N($R^7$)$R^8$ or, together with $R^5$ and the nitrogen atom to which both are bound, morpholino, pyrrolidino, piperidino, hexahydroazepin-1-yl, piperazin-1-yl which is optionally substituted in the 4-position by methyl, ethyl or benzyl, 2,4-dimethylpiperazine-1-yl or hexahydro-1H-1,4-diazepin-1-yl substituted in the 4-position by methyl or ethyl,
$R^7$ denotes alkyl with from 1 to 4 carbon atoms,
$R^8$ denotes alkyl with from 1 to 4 carbon atoms,
A denotes straight-chain or branched alkylene with from 1 to 5 carbon atoms and
m denotes 2 or 3,
or an acid-addition salt thereof.

2. A pyrazolobenzodiazepinone or an acid-addition salt according to claim 1 wherein
$R^1$ denotes methyl or ethyl,
$R^2$ denotes a hydrogen atom, methyl or ethyl,
$R^3$ denotes a hydrogen atom or —CO—A—$R^4$,
$R^4$ denotes chloro and
A denotes straight-chain or branched alkylene with 1 or 2 carbon atoms.

3. A compound according to claim 2 in which A denotes methylene.

4. A compound according to claim 2 in which $R^1$ denotes methyl, $R^2$ denotes a hydrogen atom or methyl or ethyl and $R^3$ denotes a hydrogen atom or —CO—$CH_2$—Cl, or an acid-addition salt thereof.

5. A pyrazolobenzodiazepinone or an acid-addition salt according to claim 1 wherein
$R^1$ denotes methyl or ethyl,
$R^2$ denotes a hydrogen atom, methyl or ethyl,
$R^3$ denotes —CO—A—$R^4$,
$R^4$ denotes —N($R^5$)$R^6$,
$R^5$ denotes alkyl with from 1 to 4 carbon atoms, alkenyl with 3 or 4 carbon atoms or, together with $R^6$ and the nitrogen atom to which both are bound, morpholino, pyrrolidino, piperidino, hexahydroazepin-1-yl, piperazin-1-yl which is substituted in the 4-position by methyl, ethyl or benzyl, 2,4-dimethylpiperazin-1-yl or hexahydro-1H-1,4-diazepin-1-yl which is substituted in the 4-position by methyl or ethyl, $R^6$ has one of the meanings of $R^5$, is $-(CH_2)_3-N(R^7)R^8$ or, together with $R^5$ and the nitrogen atom to which both are bound, denotes morpholino, pyrrolidino, piperidino, hexahydroazepin-1-yl, piperazin-1-yl which is substituted in the 4-position by methyl, ethyl or benzyl, 2,4-dimethylpiperazin-1-yl or hexahydro-1H-1,4-diazepin-1-yl which is substituted in the 4-position by methyl or ethyl, $R^7$ denots methyl or ethyl, $R^8$ denotes methyl or ethyl, m denotes 2 or 3 and A denotes straight-chain or branched alkylene with 1 or 2 carbon atoms.

6. A compound according to claim 5 (in which $R^1$ denotes methyl or ethyl; $R^2$ denotes a hydrogen atom, methyl or ethyl; $R^5$ denotes methyl or ethyl, or, together with $R^6$ and the nitrogen atom to which both are bound, pyrrolidino, piperidino or hexahydroazepin-1-yl; $R^6$ has the meaning of $R^5$, is $-(CH_2)_m-N(R^7)R^8$ or, together with $R^5$ and the nitrogen atom to which both are bound, is pyrrolidino, piperidino or hexahydroazepin-1-yl; each of $R^7$ and $R^8$ is, independently, methyl or ethyl; m denotes 2; and A denotes methylene) or a pharmacologically-acceptable acid-addition salt thereof.

7. A compound according to claim 5 (in which $R^1$ denotes methyl or ethyl; $R^2$ denotes a hydrogen atom, methyl or ethyl; $R^5$ and $R^6$, together with the nitrogen atom to which both are bound, denote piperazin-1-yl which is substituted in the 4-position by methyl, ethyl or benzyl, 2,4-dimethylpiperazin-1-yl or hexahydro-1H-1,4-diazepin-1-yl which is substituted in the 4-position by methyl or ethyl; and A denotes methylene) or a pharmacologically-acceptable acid-addition salt thereof.

8. A compound according to claim 5 (in which $R^1$ denotes methyl or ethyl; $R^2$ denotes a hydrogen atom, methyl or ethyl; $R^5$ and $R^6$, together with the nitrogen atom to which both are bound, denote piperazin-1-yl which is substituted in the 4-position by methyl; and A denotes methylene) or a pharmacologically-acceptable acid-addition salt thereof.

9. The compound according to claim 5 in which each of $R^1$ and $R^2$ denotes methyl; $R^5$ and $R^6$, together with the nitrogen atom to which both are bound, denote piperazin-1-yl which is substituted in the 4-position by methyl; and A denotes methylene; or a pharmacologically-acceptable acid-addition salt thereof.

10. The compound according to claim 5 in which $R^1$ is methyl, $R^2$ denotes hydrogen; $R^5$ and $R^6$, together with the nitrogen atom to which both are bound, denote piperazin-1-yl which is substituted in the 4-position by methyl; and A denotes methylene; or a pharmacologically-acceptable acid-addition salt thereof.

11. A pyrazolobenzodiazepinone according to claim 1 wherein $R^1$ denotes alkyl with from 1 to 4 carbon atoms, $R^2$ denotes a hydrogen atom (—H) or alkyl with from 1 to 4 carbon atoms, $R^3$ denotes $-CO-A-R^4$, $R^4$ denotes $-N(R^5)R^6$, $R^5$ denotes alkyl with from 1 to 4 carbon atoms, alkenyl with from 3 to 5 carbon atoms or, together with $R^6$ and the nitrogen atom to which both are bound, morpholino, pyrrolidino, piperidino, hexahydroazepin-1-yl, piperazin-1-yl which is optionally substituted in the 4-position by methyl, ethyl or benzyl, 2,4-dimethylpiperazin-1-yl or hexahydro-1H-1,4-diazepin-1-yl substituted in the 4-position by methyl or ethyl, $R^6$ has one of the meanings of $R^5$, is $-(CH_2)_m-N(R^7)R^8$, or, together with $R^5$ and the nitrogen atom to which both are bound, is morpholino, pyrrolidino, piperidino, hexahydroazepin-1-yl, piperazin-1-yl which is optionally substituted in the 4-position by methyl, ethyl or benzyl, 2,4-dimethylpiperazin-1-yl or hexahydro-1H-1,4-diazepin-1-yl substituted in the 4-position by methyl or ethyl, $R^7$ denotes alkyl with from 1 to 4 carbon atoms, $R^8$ denotes alkyl with from 1 to 4 carbon atoms, A denotes straight-chain or branched alkylene with from 1 to 5 carbon atoms and m denotes 2 or 3, or a pharmacologically-acceptable acid-addition salt thereof.

12. A medicament composition useful for the prophylaxis or treatment of stomach or intestinal disorders comprising pharmaceutical excipient and from 0.5 to 95 percent by weight of at least one compound according to claim 11.

13. A medicament composition for the prophylaxis or treatment of stomach or intestinal disorders which comprises pharmaceutical excipient and an effective concentration of at least one compound according to claim 11.

14. A medicament composition useful for the prophylaxis or treatment of stomach or intestinal disorders comprising pharmaceutical excipient and from 0.5 to 100 milligrams per unit dose of at least one compound according to claim 11.

15. A method of preventing, reducing the severity of or treating stomach or intestinal disorders which comprises administering an effective amount of a compound according to claim 11 to a mammal prone to or afflicted with such disorders.

* * * * *

UNITED STATES PATENT AND TRADEMARK OFFICE
CERTIFICATE OF CORRECTION

PATENT NO. : 4,317,823

DATED : March 2, 1982

INVENTOR(S) : Georg RAINER

Page 1 of 2

It is certified that error appears in the above-identified patent and that said Letters Patent are hereby corrected as shown below:

Title page, right column, item [56], "Sweet et al." should read --Swett et al.--. Column 2, in the formula, "2N," should read --2N--. Column 3, line 20, "representative" should read --representatives--; line 55, "R1" should read --$R^1$--. Column 4, line 46, "N-ethyl-n-" should read --N-ethyl-N- --. Column 5, line 11, "[1,5-" should read --[1,5]--; line 58, "N(2" should read --N-(2--; line 65, "4-[hexahydroazepin" should read --4-[(hexahydroazepin--. Column 8, line 30, "ministration" should read --ministrations--. Column 9, line 47, "pharmaceutically" should read --pharmacologically--; line 60, "antiacids" should read --antacids--. Column 10, line 7, "sudoxicum" should read --sudoxicam--. Column 10, line 50, in the formula, "N," should read --N--. Column 14, in the formula, "N," should read --N--. Column 16, line 21, "2 N" should read --2N--; line 38, "[1,5]-" should read --[1,5]--. Column 19, line 64, "198,5° to 200,5°" should read --198.5° to 200.5°--. Column 20, line 33, "[1,5 benzodiaze-" should read --[1,5]benzodiaze- --. Column 21, line 9, "chloropropionyl-" should read --chloropropionyl)- --. Column 22, line 3, "1methyl" should read --1-methyl--; line 10, "[B 4,3-b]" should read --[4,3-b]; line 15, "4(5" should read --4-(5--. Column 23, line 36, "dropyazolo" should read --dropyrazolo--. Column 24, line 42, "10 one" should read --10-one--; line 58, "dropyrazolo-" should read --dropyrazolo--. Column 27, line 35, "[1,5-" should read --[1,5]--. Column 29, line 55, "pyrazol" should read --pyrazole--. Column 34, line 26, "carboxyl" should read --carbonyl--; line 30, "N,N,-" should read --N,N- --. Column 35, line 44, "isopropyl-1-methylpyrazole" should read --isopropylpyrazole--; line 47, "diemthyl" should read --dimethyl--. Column 36, line 21, "[1,4]" should read

UNITED STATES PATENT AND TRADEMARK OFFICE
CERTIFICATE OF CORRECTION

PATENT NO. : 4,317,823

DATED : March 2, 1982

INVENTOR(S) : Georg RAINER

It is certified that error appears in the above-identified patent and that said Letters Patent are hereby corrected as shown below:

--[1,5]--; lines 22 and 33, "to 812" should read --812--; line 45, "--" should read -- -1--. Column 38, line 32, "piperazine" should read --piperazin--. Column 39, line 2, ")₃" should read --)$_m$--; line 10, "denots" should read --denotes--.

Signed and Sealed this

Tenth Day of August 1982

[SEAL]

Attest:

GERALD J. MOSSINGHOFF

Attesting Officer

Commissioner of Patents and Trademarks